(12) United States Patent
Smith et al.

(10) Patent No.: US 8,142,783 B2
(45) Date of Patent: Mar. 27, 2012

(54) METHODS OF TREATING AN INFLAMMATORY CONDITION INVOLVING VAP-1-MEDIATED ADHESION WITH VAP-1-SPECIFIC ANTIBODIES

(75) Inventors: David John Smith, Naantali (FI); Petri Vainio, Turku (FI); Jari Mikkola, Turku (FI); Päivi Vuorio, Turku (FI); Jani Vainio, Halikko (FI)

(73) Assignee: Biotie Therapies Corp., Turku (FI)

( * ) Notice: Subject to any disclaimer, the term of this patent is extended or adjusted under 35 U.S.C. 154(b) by 0 days.

(21) Appl. No.: 12/940,476

(22) Filed: Nov. 5, 2010

(65) Prior Publication Data

US 2011/0117021 A1    May 19, 2011

Related U.S. Application Data

(62) Division of application No. 12/081,707, filed on Apr. 18, 2008, now Pat. No. 7,897,149.

(60) Provisional application No. 60/907,904, filed on Apr. 20, 2007.

(30) Foreign Application Priority Data

Apr. 20, 2007  (FI) ................................. 20075278

(51) Int. Cl.
*A61K 39/395*  (2006.01)
(52) U.S. Cl. ............... 424/144.1; 424/130.1; 424/133.1; 424/141.1; 424/142.1; 424/143.1; 424/152.1; 424/172.1
(58) Field of Classification Search .................... None
See application file for complete search history.

(56) References Cited

U.S. PATENT DOCUMENTS

| | | | |
|---|---|---|---|
| 5,580,780 A | 12/1996 | Jalkanen et al. | |
| 7,897,149 B2 | 3/2011 | Smith et al. | |

FOREIGN PATENT DOCUMENTS

| | | |
|---|---|---|
| WO | WO-93/25582 A1 | 12/1993 |
| WO | WO-98/53049 A1 | 11/1998 |
| WO | WO-03/084469 A2 | 10/2003 |
| WO | WO-03/093319 A1 | 11/2003 |

OTHER PUBLICATIONS

Rudikoff, S. et al., "Single amino acid substitution altering antigen-binding specificity", Proc Natl Acad Sci USA, Mar. 1982, vol. 79, pp. 1979-1983.
Colman, P.M., "Effects of amino acid sequence changes on antibody-antigen interactions," Research in Immunology, 1994, vol. 145, pp. 33-36.
Kussie, P.H., "A Single Engineered Amino Acid Substitution Changes Antibody Fine Specificity," J. Immunol., 1994, vol. 152, pp. 146-152.
Chen, C., et al., "Enhancement and destruction of antibody function by somatic mutation: unequal occurrence is controlled by V gene combinatorial associations," EMBO J., 1995, vol. 14, No. 12, pp. 2784-2794.
Bendig, M. M., "Humanization of Rodent Monoclonal Antibodies by CDR Grafting," Methods: A Companion to Methods in Enzymology, 1995, vol. 8, pp. 83-93.
Padlan, E. A., "Structure of an antibody-antigen complex: Crystal structure of the HyHEL-10 Fab-lysozyme complex," Proc. Natl. Acad. Sci. USA, Aug. 1989, vol. 86, pp. 5938-5942.
Kirton, C. M. et al., "Function-blocking antibodies to human vascular adhesion protein-1: A potential anti-inflammatory therapy," Eur. J. Immunol., 2005, vol. 35, pp. 3119-3130, VCH Verlagsgesellschaft.
Kurkijärvi, R. et al., "Circulating Form of Human Vascular Adhesion Protein-1 (VAP-1): Increased Serum Levels in Inflammatory Liver Diseases," J. Immunol., 1998, vol. 161; pp. 1549-1557, American Association of Immunologists.
Van Dijik, M. A. et al., "Human antibodies as next generation therapeutics," Curr. Opin. Chem. Biol., 2001, vol. 5, pp. 368-374, Current Biology.
International Search Report for International Application No. PCT/FI2008/050199, mailed on Jul. 29, 2008, National Board of Patents and Registration of Finland, Helsinki, FI.

*Primary Examiner* — Phillip Gambel
(74) *Attorney, Agent, or Firm* — Birch, Stewart, Kolasch & Birch, LLP

(57) ABSTRACT

Novel fully human anti-VAP-1 antibodies and fragments thereof are disclosed. Nucleic acids encoding anti-VAP-1 antibodies or fragments thereof, as well as expression vectors and host cells incorporating these nucleic acids for the recombinant expression of anti-VAP-1 antibodies are also given. Pharmaceutical compositions comprising said antibodies and therapeutic uses thereof are also disclosed.

11 Claims, 10 Drawing Sheets

8C10 V_L

```
  1 V  I  Q  L  T  Q  S  P  S  S  L  S  A  S  V  G  D  R  V  T
  1 gtcatccagttgacccagtctccatcctccctgtctgcatctgtaggagacagagtcacc
 21 I  T  C  R  A  S  Q  G  I  S  R  A  L  A  W  Y  Q  Q  K  P
 61 atcacttgccgggcaagtcagggcattagcagggctttagcctggtatcagcagaaacca
 41 G  K  P  K  L  L  I  Y  D  A  S  S  L  E  S  G  V  P  S
121 gggaaaggtcctaagctcctgatctatgatgcctccagtttggaaagtggggtcccatca
 61 R  F  S  G  S  G  S  G  T  D  F  T  L  T  I  S  S  L  Q  P
181 aggttcagcggcagtggatctgggacagatttcactctcaccatcagcagcctgcagcct
 81 E  D  F  A  T  Y  Y  C  Q  Q  F  N  S  Y  P  L  T  F  G  G
241 gaagattttgcaacttattactgtcaacagtttaatagttaccctctcactttcggcgga
101 G  T  K  V  E  I  K
301 gggaccaaggtggagatcaaa
```

```
  1 Q  V  Q  L  V  E  S  G  G  G  V  V  Q  P  G  R  S  L  R  L
  1 caggtgcaactggtggagtctgggggaggcgtggtccagcctgggaggtccctgagactc
 21 S  C  A  A  S  G  F  T  F  F  S  Y  A  M  H  W  V  R  Q  T
 61 tcctgtgcagcgtctggattcaccttctttagctatgccatgcactgggtccgccagact
 41 P  G  K  G  L  E  W  V  A  V  I  W  F  D  G  S  N  E  N  Y
121 ccaggcaagggcctggagtgggtggcagttatatggtttgatggaagtaatgaaaactat
 61 V  D  S  V  K  G  R  F  T  I  S  R  D  N  S  K  N  T  L  Y
181 gtagactccgtgaagggccgattcaccatctccagagacaattccaagaacacgctgtat
 81 L  Q  M  N  T  L  R  A  E  D  T  A  V  Y  Y  C  A  R  D  A
241 ctgcaaatgaacaccctgagagccgaggacacggctgtgtattactgtgcgagagatgcc
101 W  S  Y  F  D  Y  W  G  Q  G  T  L  V  T  V  S  S
301 tggagctactttgactactggggccagggaaccctggtcaccgtctcctca
```

```
  1 E   I   V   L   T   Q   S   P   A   T   L   S   L   S   P   G   E   R   A   T
  1 gaaattgtgttgacacagtctccagccaccctgtctttgtctccaggggaaagagccacc
 21 L   S   C   R   A   S   Q   S   V   S   S   Y   L   A   W   Y   Q   Q   K   P
 61 ctctcctgcagggccagtcagagtgttagcagctacttagcctggtaccaacagaaacct
 41 G   Q   A   P   R   L   L   I   Y   D   A   S   N   R   A   T   G   I   P   A
121 ggccaggctcccaggctcctcatctatgatgcatccaacagggccactggcatcccagcc
 61 R   F   S   G   S   G   S   G   T   D   F   T   L   T   I   S   S   L   E   P
181 aggttcagtggcagtgggtctgggacagacttcactctcaccatcagcagcctagagcct
 81 E   D   F   A   V   Y   Y   C   Q   Q   R   S   N   W   P   L   T   F   G   G
241 gaagattttgcagtttattactgtcagcagcgtagcaactggccgctcactttcggcgga
101 G   T   K   V   E   I   K
301 gggaccaaggtggagatcaaa
```

```
  1 E   V   Q   L   V   E   S   G   G   G   L   V   Q   P   G   G   S   L   R   L
  1 gaggtgcagctggtggagtctggggggaggcttggtccagcctggggggtccctgagactc
 21 S   C   A   A   S   G   F   I   F   S   N   Y   W   M   S   W   V   R   Q   A
 61 tcctgtgcagcctctggattcatttttcagtaactattggatgagctgggtccgccaggct
 41 P   G   K   G   L   E   W   V   A   N   I   K   Q   D   G   S   E   K   Y   Y
121 ccagggaagggctggagtgggtggccaacataaagcaagatggaagtgagaagtactat
 61 V   D   S   V   R   G   R   F   T   V   S   R   D   N   A   K   N   S   L   Y
181 gtggactctgtgaggggccgattcaccgtctccagagacaacgccaagaactcactgtat
 81 L   Q   M   N   S   L   R   A   E   D   T   A   V   Y   Y   C   A   R   D   Y
241 ctgcaaatgaacagcctgagagccgaggacacggctgtgtattactgtgcgagggattac
101 F   G   S   G   T   Y   F   F   Y   F   D   Y   W   G   Q   G   T   L   V   T
301 tttggttcggggacttatttcttctactttgactactggggccagggaaccctggtcacc
121 F   S   S
361 ttctcctca
```

```
  1 A  I  Q  L  T  Q  S  P  S  S  L  S  A  S  V  G  D  R  V  T
  1 gccatccagttgacccagtctccatcctccctgtctgcatctgtaggagacagagtcacc
 21 I  T  C  R  A  S  Q  G  I  S  R  A  L  A  W  Y  Q  Q  K  P
 61 atcacttgccgggcaagtcagggcattagcagagctttagcctggtatcagcagaaacca
 41 G  K  A  P  K  L  L  I  Y  D  A  S  N  L  E  R  G  V  P  S
121 gggaaagctcctaagctcctgatctatgatgcctccaatttggaaagaggggtcccatca
 61 R  F  S  G  S  G  S  G  T  D  F  T  L  T  I  S  S  L  Q  P
181 aggttcagcggcagtggatctgggacagatttcactctcaccatcagcagcctgcaacct
 81 E  D  F  A  T  Y  Y  C  Q  Q  F  N  S  F  P  L  T  F  G  G
241 gaggattttgcaacttattactgtcaacagtttaatagtttcccgctcactttcggcgga
101 G  T  K  V  E  I  K
301 gggaccaaggtggagatcaaa
```

```
  1 Q  V  Q  L  V  E  S  G  G  G  V  V  Q  P  G  R  S  L  R  L
  1 caggtgcagctggtggagtctgggggaggcgtggtccagcctggaggtccctgagactc
 21 S  C  A  A  S  G  F  T  F  S  S  Y  A  M  H  W  V  R  Q  A
 61 tcctgtgcagcgtctggattcaccttcagtagctatgccatgcactgggtccgccaggct
 41 P  G  K  G  L  E  W  V  A  V  L  W  F  D  G  S  N  E  D  Y
121 ccaggcaaggggctggagtgggtggcagtttatggtttgatggaagtaatgaagactat
 61 A  D  S  V  K  G  R  F  T  I  S  R  D  N  S  K  N  T  L  Y
181 gcagactccgtgaagggccgattcaccatctccagagacaactccaagaacacgctgtat
 81 L  Q  M  N  S  L  R  A  E  D  T  A  V  Y  Y  C  A  R  D  G
241 ctgcaaatgaacagcctgagagccgaggacacggctgtgtattactgtgcgagagatggc
101 W  G  Y  F  D  Y  W  G  Q  G  T  L  V  T  V  S  S
301 tggggatactttgactactggggccagggaaccctggtcaccgtctcctca
```

```
  1 D  I  Q  M  T  Q  S  P  S  S  L  S  A  S  V  G  D  R  V  T
  1 gacatccagatgacccagtctccatcctcactgtctgcatctgtaggagacagagtcacc
 21 I  T  C  R  A  S  Q  G  I  S  S  W  L  A  W  Y  Q  Q  K  P
 61 atcacttgtcgggcgagtcagggtattagcagctggttagcctggtatcagcagaaacca
 41 E  K  A  P  K  S  L  I  Y  G  A  S  S  L  Q  S  G  V  P  S
121 gagaaagcccctaagtccctgatctatggtgcatccagtttgcaaagtggggtcccatca
 61 R  F  S  G  S  G  S  G  T  D  F  T  L  T  I  S  S  L  Q  P
181 aggttcagcggcagtggatctgggacagatttcactctcaccatcagcagcctgcagcct
 81 E  D  F  A  T  Y  Y  C  Q  Q  Y  N  S  Y  P  R  T  F  G  Q
241 gaagattttgcaacttattactgccaacagtataatagttaccctcggacgttcggccaa
101 G  T  K  V  E  I  K
301 gggaccaaggtggaaatcaaa
```

```
  1 Q  V  Q  L  V  D  S  G  G  D  V  V  Q  P  G  R  S  L  R  L
  1 caggtgcagctggtggactctgggggagacgtggtccagcctgggaggtccctgagactc
 21 S  C  A  A  S  G  F  S  F  S  R  S  G  I  H  W  V  R  Q  A
 61 tcctgtgcagcgtctggattcagtttcagtcggtctggcatacactgggtccgccaggct
 41 P  G  K  G  L  E  W  V  A  V  I  W  Y  D  G  I  Y  K  Y  Y
121 ccaggcaagggggctggagtgggtggcagttatatggtatgatggaatttataagtactat
 61 A  D  S  V  K  G  R  F  T  I  S  R  D  N  S  K  N  T  L  Y
181 gcagactccgtgaagggccgattcaccatctccagagacaattccaagaacacgctgtat
 81 L  Q  M  N  S  L  R  A  E  D  T  A  V  Y  Y  C  A  R  E  K
241 ctgcaaatgaacagcctgagggccgaggacacggctgtgtattactgtgcgagagagaag
101 N  W  G  I  D  Y  W  G  Q  G  T  L  V  T  V  S  S
301 aactggggaattgactactggggccagggaaccctggtcaccgtctcctca
```

```
  1 E   I   V   L   T   Q   S   P   G   T   L   S   L   S   P   G   D   R   A   T
  1 gaaattgtgttgacgcagtctccaggcaccctgtctttgtctccaggggatagagccacc
 21 L   S   C   R   A   S   Q   S   V   S   S   S   F   L   A   W   Y   Q   Q   K
 61 ctctcctgcagggccagtcagagtgttagcagcagcttcttagcctggtaccagcagaaa
 41 P   G   Q   A   P   R   L   L   I   Y   G   A   S   S   R   A   T   G   I   P
121 cctggccaggctcccaggctcctcatctatggtgcatccagcagggccactggcatccca
 61 D   R   F   S   G   S   G   S   G   T   D   F   T   L   T   I   S   R   L   E
181 gacaggttcagtggcagtgggtctgggacagacttcactctcaccatcagcagactggag
 81 P   E   D   F   A   V   Y   Y   C   Q   Q   Y   G   S   S   P   L   T   F   G
241 cctgaagatttgcagtgtattactgtcagcagtatggtagctcaccgctcactttcggc
101 G   G   T   K   V   E   I   K
301 ggagggaccaaggtggagatcaaa
```

```
  1 E   V   Q   L   V   Q   S   G   G   G   L   V   H   P   G   G   S   L   R   L
  1 gaggttcagctggtgcagtctgggggaggcttggtacatccgggggggtccctgagactc
 21 S   C   A   G   S   G   F   P   V   S   S   Y   G   M   H   W   V   R   Q   A
 61 tcctgtgcaggctctggattccccgtcagtagctatggaatgcactgggttcgccagct
 41 P   G   K   G   L   E   W   V   S   A   I   G   V   G   G   T   Y   H   V
121 ccaggaaaaggtctggagtgggtatcagctattggtgttggtggtggcacataccatgta
 61 D   S   V   K   G   R   F   T   I   S   R   D   N   A   K   N   S   L   Y   L
181 gattccgtgaagggccgattcaccatctccagagacaatgccaagaactccttgtatctt
 81 Q   M   N   S   L   R   A   G   D   M   A   V   Y   Y   C   A   R   D   P   G
241 caaatgaacagcctgagagccgggacatggctgtgtattactgtcaagagatcctggg
101 F   G   E   V   Y   F   D   Y   W   G   Q   G   T   L   V   T   V   S   S
301 ttcggggaggtctactttgactattggggccagggaaccctggtcaccgtctcctca
```

Fig. 5B

V_H sequences

```
                    1                                                 50
8C10.V_H    (1)  QVQLVESGGGVVQPGRSLRLSCAASGFTFFSYAMHWVRQTPGKGLEWVAV
8A4.V_H     (1)  EVQLVESGGGLVQPGGSLRLSCAASGFIFSNYWMSWVRQAPGKGLEWVAN
3F10.V_H    (1)  QVQLVESGGGVVQPGRSLRLSCAASGFTFSSYAMHWVRQAPGKGLEWVAV
5F12.V_H    (1)  QVQLVDSGGDVVQPGRSLRLSCAASGFSFSRSGIHWVRQAPGKGLEWVAV
4B3.V_H     (1)  EVQLVQSGGGLVHPGGSLRLSCAGSGFPVSSYGMHWVRQAPGKGLEWVSA
Consensus   (1)  QVQLVESGGGVVQPGRSLRLSCAASGFTFSSYAMHWVRQAPGKGLEWVAV 51                                                100
8C10.V_H    (51) IWFDGSNENYVDSVKGRFTISRDNSKNTLYLQMNTLRAEDTAVYYCARDA
8A4.V_H     (51) IKQDGSEKYYVDSVRGRFTVSRDNAKNSLYLQMNSLRAEDTAVYYCARDY
3F10.V_H    (51) LWFDGSNEDYADSVKGRFTISRDNSKNTLYLQMNSLRAEDTAVYYCARDG
5F12.V_H    (51) IWYDGIYKYYADSVKGRFTISRDNSKNTLYLQMNSLRAEDTAVYYCAREK
4B3.V_H     (51) IGVGG-TYHVDSVKGRFTISRDNAKNSLYLQMNSLRAGDMAVYYCARDP
Consensus   (51) IWFDGS  YYVDSVKGRFTISRDNSKNTLYLQMNSLRAEDTAVYYCARD 101            123
8C10.V_H   (101) W------SYFDYWGQGTLVTVSS
8A4.V_H    (101) FGSGTYFFYFDYWGQGTLVTFSS
3F10.V_H   (101) W------GYFDYWGQGTLVTVSS
5F12.V_H   (101) N------WGIDYWGQGTLVTVSS
4B3.V_H    (100) GFG---EVYFDYWGQGTLVTVSS
Consensus  (101) W      YFDYWGQGTLVTVSS
```

Fig. 6A

```
CDR1
                  31
8C10.V_H    (31) SYAMH
8A4.V_H     (31) NYWMS
3F10.V_H    (31) SYAMH
5F12.V_H    (31) RSGIH
4B3.V_H     (31) SYGMH
Consensus   (31) SYAMH
```

Fig. 6B

```
CDR2
                  50            66
8C10.V_H    (50) VIWFDGSNENYVDSVKG
8A4.V_H     (50) NIKQDGSEKYYVDSVRG
3F10.V_H    (50) VLWFDGSNEDYADSVKG
5F12.V_H    (50) VIWYDGIYKYYADSVKG
4B3.V_H     (50) AIGVGG-TYHVDSVKG
Consensus   (50) VIWFDGS  YYVDSVKG
```

Fig. 6C

CDR3

```
                  99              112
8C10.V_H    (99)  DAW------SYFDY
8A4.V_H     (99)  DYFGSGTYFFYFDY
3F10.V_H    (99)  DGW------GYFDY
5F12.V_H    (99)  EKN------WGIDY
4B3.V_H     (98)  DPGFG---EVYFDY
Consensus   (99)  D W          YFDY
```

Fig. 6D

V_l sequences

```
                   1                                                50
8C10.V_L    (1)   VIQLTQSPSSLSASVGDRVTITCRASQGIER-ALAWYQQKPGKAPKLLIY
8A4.V_L     (1)   EIVLTQSPATLSLSPGERAPLSCRASQSVSS-YLAWYQQKPGQAPRLLIY
3F10.V_L    (1)   AIQLTQSPSSLSASVGDRVTITCRASQGIER-ALAWYQQKPGKAPKLLIY
5F12.V_L    (1)   DIQMTQSPSSLSASVGDRVTITCRASQGISS-WLAWYQQKPEKAPKSLIY
4B3.V_L     (1)   EIVLTQSPGTLSLSPGDRATLSCRASQSVSSSFLAWYQQKPGQAPRLLIY
Consensus   (1)   EIQLTQSPSSLSASVGDRVTITCRASQGISS FLAWYQQKPGKAPKLLIY 51                                              100
8C10.V_L    (50)  DASSLESGVPSRFSGSGSGTDFTLTISSLQPEDFATYYCQQFNSYPLTFG
8A4.V_L     (50)  DASNRATGIPARFSGSGSGTDFTLTISSLEPEDFAVYYCQQRSNWPLTFG
3F10.V_L    (50)  DASNLERGVPSRFSGSGSGTDFTLTISSLQPEDFATYYCQQFNSFPLTFG
5F12.V_L    (50)  GASSLQSGVPSRFSGSGSGTDFTLTISSLQPEDFATYYCQQYNSYFRTFG
4B3.V_L     (51)  GASSRATGIPDRFSGSGSGTDFTLTISRLEPEDFAVYYCQQYGSSPLTFG
Consensus   (51)  DASSL SGVPSRFSGSGSGTDFTLTISSLQPEDFATYYCQQFNSYPLTFG 101
8C10.V_L    (100) GGTKVEIK
8A4.V_L     (100) GGTKVEIK
3F10.V_L    (100) GGTKVEIK
5F12.V_L    (100) QGTKVEIK
4B3.V_L     (101) GGTKVEIK
Consensus   (101) GGTKVEIK
```

Fig. 6E

CDR1

```
                  24
8C10.V_L    (24)  RASQGISR-ALA
8A4.V_L     (24)  RASQSVSS-YLA
3F10.V_L    (24)  RASQGISR-ALA
5F12.V_L    (24)  RASQGISS-NLA
4B3.V_L     (24)  RASQSVSSFLA
Consensus   (24)  RASQGISS FLA
```

Fig. 6F

CDR2

```
                  51
8C10.V_L    (50)  DASSLES
8A4.V_L     (50)  DASNRAT
3F10.V_L    (50)  DASNLER
5F12.V_L    (50)  GASSLQS
4B3.V_L     (51)  GASSRAT
Consensus   (51)  DASSL S
```

Fig. 6G

CDR3

```
                  90
8C10.V_L    (89)  QQFNSYPLT
8A4.V_L     (89)  QQRSNWPLT
3F10.V_L    (89)  QQFNSFPLT
5F12.V_L    (89)  QQYNSYPRT
4B3.V_L     (90)  QQYGSSPLT
Consensus   (90)  QQFNSYPLT
```

Fig. 6H

SEQUENCE LISTING

```
<160> NUMBER OF SEQ ID NOS: 90

<210> SEQ ID NO 1
<211> LENGTH: 5
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: S, N or R
<220> FEATURE:
<221> NAME/KEY: MISC_FEATURE
<222> LOCATION: (2)..(2)
<223> OTHER INFORMATION: Y or S
<220> FEATURE:
<221> NAME/KEY: MISC_FEATURE
<222> LOCATION: (3)..(3)
<223> OTHER INFORMATION: A, G or W
<220> FEATURE:
<221> NAME/KEY: MISC_FEATURE
<222> LOCATION: (4)..(4)
<223> OTHER INFORMATION: M or I
<220> FEATURE:
<221> NAME/KEY: MISC_FEATURE
<222> LOCATION: (5)..(5)
<223> OTHER INFORMATION: H or S

<400> SEQUENCE: 1

Xaa Xaa Xaa Xaa Xaa
1               5

<210> SEQ ID NO 2
<211> LENGTH: 17
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: V, A or N
<220> FEATURE:
<221> NAME/KEY: MISC_FEATURE
<222> LOCATION: (2)..(2)
<223> OTHER INFORMATION: I or L
<220> FEATURE:
<221> NAME/KEY: MISC_FEATURE
```

```
<222> LOCATION: (3)..(3)
<223> OTHER INFORMATION: W, G or K
<220> FEATURE:
<221> NAME/KEY: MISC_FEATURE
<222> LOCATION: (4)..(4)
<223> OTHER INFORMATION: F, Q, V or Y
<220> FEATURE:
<221> NAME/KEY: MISC_FEATURE
<222> LOCATION: (5)..(5)
<223> OTHER INFORMATION: D or G
<220> FEATURE:
<221> NAME/KEY: MISC_FEATURE
<222> LOCATION: (7)..(7)
<223> OTHER INFORMATION: S, G or I
<220> FEATURE:
<221> NAME/KEY: MISC_FEATURE
<222> LOCATION: (8)..(8)
<223> OTHER INFORMATION: N, E, Y or no amino acid
<220> FEATURE:
<221> NAME/KEY: MISC_FEATURE
<222> LOCATION: (9)..(9)
<223> OTHER INFORMATION: E, K or T
<220> FEATURE:
<221> NAME/KEY: MISC_FEATURE
<222> LOCATION: (10)..(10)
<223> OTHER INFORMATION: Y, D or N
<220> FEATURE:
<221> NAME/KEY: MISC_FEATURE
<222> LOCATION: (11)..(11)
<223> OTHER INFORMATION: Y or H
<220> FEATURE:
<221> NAME/KEY: MISC_FEATURE
<222> LOCATION: (12)..(12)
<223> OTHER INFORMATION: V or A
<220> FEATURE:
<221> NAME/KEY: MISC_FEATURE
<222> LOCATION: (16)..(16)
<223> OTHER INFORMATION: K or R

<400> SEQUENCE: 2

Xaa Xaa Xaa Xaa Xaa Gly Xaa Xaa Xaa Xaa Xaa Xaa Asp Ser Val Xaa
1               5                   10                  15

Gly

<210> SEQ ID NO 3
<211> LENGTH: 14
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: D or E
<220> FEATURE:
<221> NAME/KEY: MISC_FEATURE
<222> LOCATION: (2)..(2)
<223> OTHER INFORMATION: A, G, K, P or Y
<220> FEATURE:
<221> NAME/KEY: MISC_FEATURE
<222> LOCATION: (3)..(3)
<223> OTHER INFORMATION: W, F, G or N
<220> FEATURE:
<221> NAME/KEY: MISC_FEATURE
<222> LOCATION: (4)..(4)
<223> OTHER INFORMATION: F, G or no amino acid
<220> FEATURE:
<221> NAME/KEY: MISC_FEATURE
<222> LOCATION: (5)..(5)
<223> OTHER INFORMATION: G, S or no amino acid
<220> FEATURE:
<221> NAME/KEY: MISC_FEATURE
<222> LOCATION: (6)..(6)
<223> OTHER INFORMATION: G or no amino acid
<220> FEATURE:
<221> NAME/KEY: MISC_FEATURE
<222> LOCATION: (7)..(7)
<223> OTHER INFORMATION: T or no amino acid
<220> FEATURE:
```

```
<221> NAME/KEY: MISC_FEATURE
<222> LOCATION: (8)..(8)
<223> OTHER INFORMATION: Y or no amino acid
<220> FEATURE:
<221> NAME/KEY: MISC_FEATURE
<222> LOCATION: (9)..(9)
<223> OTHER INFORMATION: E, F or no amino acid
<220> FEATURE:
<221> NAME/KEY: MISC_FEATURE
<222> LOCATION: (10)..(10)
<223> OTHER INFORMATION: F, G, S, V or W
<220> FEATURE:
<221> NAME/KEY: MISC_FEATURE
<222> LOCATION: (11)..(11)
<223> OTHER INFORMATION: Y or G
<220> FEATURE:
<221> NAME/KEY: MISC_FEATURE
<222> LOCATION: (12)..(12)
<223> OTHER INFORMATION: F or I

<400> SEQUENCE: 3

Xaa Xaa Xaa Xaa Xaa Xaa Xaa Xaa Xaa Xaa Xaa Xaa Asp Tyr
1               5                   10

<210> SEQ ID NO 4
<211> LENGTH: 5
<212> TYPE: PRT
<213> ORGANISM: Homo sapiens

<400> SEQUENCE: 4

Ser Tyr Ala Met His
1               5

<210> SEQ ID NO 5
<211> LENGTH: 5
<212> TYPE: PRT
<213> ORGANISM: Homo sapiens

<400> SEQUENCE: 5

Asn Tyr Trp Met Ser
1               5

<210> SEQ ID NO 6
<211> LENGTH: 5
<212> TYPE: PRT
<213> ORGANISM: Homo sapiens

<400> SEQUENCE: 6

Ser Tyr Ala Met His
1               5

<210> SEQ ID NO 7
<211> LENGTH: 5
<212> TYPE: PRT
<213> ORGANISM: Homo sapiens

<400> SEQUENCE: 7

Arg Ser Gly Ile His
1               5

<210> SEQ ID NO 8
<211> LENGTH: 5
<212> TYPE: PRT
<213> ORGANISM: Homo sapiens

<400> SEQUENCE: 8

Ser Tyr Gly Met His
1               5
```

```
<210> SEQ ID NO 9
<211> LENGTH: 17
<212> TYPE: PRT
<213> ORGANISM: Homo sapiens

<400> SEQUENCE: 9

Val Ile Trp Phe Asp Gly Ser Asn Glu Asn Tyr Val Asp Ser Val Lys
1               5                   10                  15
Gly

<210> SEQ ID NO 10
<211> LENGTH: 17
<212> TYPE: PRT
<213> ORGANISM: Homo sapiens

<400> SEQUENCE: 10

Asn Ile Lys Gln Asp Gly Ser Glu Lys Tyr Tyr Val Asp Ser Val Arg
1               5                   10                  15
Gly

<210> SEQ ID NO 11
<211> LENGTH: 17
<212> TYPE: PRT
<213> ORGANISM: Homo sapiens

<400> SEQUENCE: 11

Val Leu Trp Phe Asp Gly Ser Asn Glu Asp Tyr Ala Asp Ser Val Lys
1               5                   10                  15
Gly

<210> SEQ ID NO 12
<211> LENGTH: 17
<212> TYPE: PRT
<213> ORGANISM: Homo sapiens

<400> SEQUENCE: 12

Val Ile Trp Tyr Asp Gly Ile Tyr Lys Tyr Tyr Ala Asp Ser Val Lys
1               5                   10                  15
Gly

<210> SEQ ID NO 13
<211> LENGTH: 16
<212> TYPE: PRT
<213> ORGANISM: Homo sapiens

<400> SEQUENCE: 13

Ala Ile Gly Val Gly Gly Gly Thr Tyr His Val Asp Ser Val Lys Gly
1               5                   10                  15

<210> SEQ ID NO 14
<211> LENGTH: 8
<212> TYPE: PRT
<213> ORGANISM: Homo sapiens

<400> SEQUENCE: 14

Asp Ala Trp Ser Tyr Phe Asp Tyr
1               5

<210> SEQ ID NO 15
<211> LENGTH: 14
<212> TYPE: PRT
<213> ORGANISM: Homo sapiens
```

<400> SEQUENCE: 15

Asp Tyr Phe Gly Ser Gly Thr Tyr Phe Tyr Phe Asp Tyr
1               5                   10

<210> SEQ ID NO 16
<211> LENGTH: 8
<212> TYPE: PRT
<213> ORGANISM: Homo sapiens

<400> SEQUENCE: 16

Asp Gly Trp Gly Tyr Phe Asp Tyr
1               5

<210> SEQ ID NO 17
<211> LENGTH: 8
<212> TYPE: PRT
<213> ORGANISM: Homo sapiens

<400> SEQUENCE: 17

Glu Lys Asn Trp Gly Ile Asp Tyr
1               5

<210> SEQ ID NO 18
<211> LENGTH: 11
<212> TYPE: PRT
<213> ORGANISM: Homo sapiens

<400> SEQUENCE: 18

Asp Pro Gly Phe Gly Glu Val Tyr Phe Asp Tyr
1               5                   10

<210> SEQ ID NO 19
<211> LENGTH: 117
<212> TYPE: PRT
<213> ORGANISM: Homo sapiens

<400> SEQUENCE: 19

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Phe Ser Tyr
                20                  25                  30

Ala Met His Trp Val Arg Gln Thr Pro Gly Lys Gly Leu Glu Trp Val
            35                  40                  45

Ala Val Ile Trp Phe Asp Gly Ser Asn Glu Asn Tyr Val Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Thr Leu Arg Ala Glu Asp Thr Ala Val Tyr Tyr Cys
                85                  90                  95

Ala Arg Asp Ala Trp Ser Tyr Phe Asp Tyr Trp Gly Gln Gly Thr Leu
            100                 105                 110

Val Thr Val Ser Ser
        115

<210> SEQ ID NO 20
<211> LENGTH: 123
<212> TYPE: PRT
<213> ORGANISM: Homo sapiens

<400> SEQUENCE: 20

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Phe Ile Phe Ser Asn Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
 50                  55                  60

Arg Gly Arg Phe Thr Val Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Asp Tyr Phe Gly Ser Gly Thr Tyr Phe Phe Tyr Phe Asp Tyr
            100                 105                 110

Trp Gly Gln Gly Thr Leu Val Thr Phe Ser Ser
            115                 120
```

<210> SEQ ID NO 21
<211> LENGTH: 117
<212> TYPE: PRT
<213> ORGANISM: Homo sapiens

<400> SEQUENCE: 21

```
Gln Val Gln Leu Val Glu Ser Gly Gly Gly Val Val Gln Pro Gly Arg
 1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Leu Trp Phe Asp Gly Ser Asn Glu Asp Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Asp Gly Trp Gly Tyr Phe Asp Tyr Trp Gly Gln Gly Thr Leu
            100                 105                 110

Val Thr Val Ser Ser
        115
```

<210> SEQ ID NO 22
<211> LENGTH: 117
<212> TYPE: PRT
<213> ORGANISM: Homo sapiens

<400> SEQUENCE: 22

```
Gln Val Gln Leu Val Asp Ser Gly Gly Asp Val Val Gln Pro Gly Arg
 1               5                   10                  15

Ser Leu Arg Leu Ser Cys Ala Ala Ser Gly Phe Ser Phe Ser Arg Ser
            20                  25                  30

Gly Ile His Trp Val Arg Gln Ala Pro Gly Lys Gly Leu Glu Trp Val
        35                  40                  45

Ala Val Ile Trp Tyr Asp Gly Ile Tyr Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95
```

```
Ala Arg Glu Lys Asn Trp Gly Ile Asp Tyr Trp Gly Gln Gly Thr Leu
            100                 105                 110

Val Thr Val Ser Ser
        115

<210> SEQ ID NO 23
<211> LENGTH: 119
<212> TYPE: PRT
<213> ORGANISM: Homo sapiens

<400> SEQUENCE: 23

Glu Val Gln Leu Val Gln Ser Gly Gly Gly Leu Val His Pro Gly Gly
1               5                   10                  15

Ser Leu Arg Leu Ser Cys Ala Gly Ser Gly Phe Pro Val Ser Ser Tyr
            20                  25                  30

Gly Met His Trp Val Arg Gln Ala Pro Gly Lys Gly Leu Glu Trp Val
        35                  40                  45

Ser Ala Ile Gly Val Gly Gly Thr Tyr His Val Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Gly Asp Met Ala Val Tyr Tyr Cys Ala
                85                  90                  95

Arg Asp Pro Gly Phe Gly Glu Val Tyr Phe Asp Tyr Trp Gly Gln Gly
            100                 105                 110

Thr Leu Val Thr Val Ser Ser
        115

<210> SEQ ID NO 24
<211> LENGTH: 12
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: G or S
<220> FEATURE:
<221> NAME/KEY: MISC_FEATURE
<222> LOCATION: (6)..(6)
<223> OTHER INFORMATION: I or V
<220> FEATURE:
<221> NAME/KEY: MISC_FEATURE
<222> LOCATION: (8)..(8)
<223> OTHER INFORMATION: S or R
<220> FEATURE:
<221> NAME/KEY: MISC_FEATURE
<222> LOCATION: (9)..(9)
<223> OTHER INFORMATION: S or no amino acid
<220> FEATURE:
<221> NAME/KEY: MISC_FEATURE
<222> LOCATION: (10)..(10)
<223> OTHER INFORMATION: A, F, W or Y

<400> SEQUENCE: 24

Arg Ala Ser Gln Xaa Xaa Ser Xaa Xaa Xaa Leu Ala
1               5                   10

<210> SEQ ID NO 25
<211> LENGTH: 7
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: D or G
<220> FEATURE:
<221> NAME/KEY: MISC_FEATURE
```

```
<222> LOCATION: (4)..(4)
<223> OTHER INFORMATION: S or N
<220> FEATURE:
<221> NAME/KEY: MISC_FEATURE
<222> LOCATION: (5)..(5)
<223> OTHER INFORMATION: L or R
<220> FEATURE:
<221> NAME/KEY: MISC_FEATURE
<222> LOCATION: (6)..(6)
<223> OTHER INFORMATION: A, E or Q
<220> FEATURE:
<221> NAME/KEY: MISC_FEATURE
<222> LOCATION: (7)..(7)
<223> OTHER INFORMATION: S, T or R

<400> SEQUENCE: 25

Xaa Ala Ser Xaa Xaa Xaa Xaa
1               5

<210> SEQ ID NO 26
<211> LENGTH: 9
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: F, Y or R
<220> FEATURE:
<221> NAME/KEY: MISC_FEATURE
<222> LOCATION: (4)..(4)
<223> OTHER INFORMATION: N, G or S
<220> FEATURE:
<221> NAME/KEY: MISC_FEATURE
<222> LOCATION: (5)..(5)
<223> OTHER INFORMATION: S or N
<220> FEATURE:
<221> NAME/KEY: MISC_FEATURE
<222> LOCATION: (6)..(6)
<223> OTHER INFORMATION: Y, F, W or S
<220> FEATURE:
<221> NAME/KEY: MISC_FEATURE
<222> LOCATION: (8)..(8)
<223> OTHER INFORMATION: L or R

<400> SEQUENCE: 26

Gln Gln Xaa Xaa Xaa Xaa Pro Xaa Thr
1               5

<210> SEQ ID NO 27
<211> LENGTH: 11
<212> TYPE: PRT
<213> ORGANISM: Homo sapiens

<400> SEQUENCE: 27

Arg Ala Ser Gln Gly Ile Ser Arg Ala Leu Ala
1               5                   10

<210> SEQ ID NO 28
<211> LENGTH: 11
<212> TYPE: PRT
<213> ORGANISM: Homo sapiens

<400> SEQUENCE: 28

Arg Ala Ser Gln Ser Val Ser Ser Tyr Leu Ala
1               5                   10

<210> SEQ ID NO 29
<211> LENGTH: 11
<212> TYPE: PRT
<213> ORGANISM: Homo sapiens

<400> SEQUENCE: 29
```

```
Arg Ala Ser Gln Gly Ile Ser Arg Ala Leu Ala
1               5                   10
```

<210> SEQ ID NO 30
<211> LENGTH: 11
<212> TYPE: PRT
<213> ORGANISM: Homo sapiens

<400> SEQUENCE: 30

```
Arg Ala Ser Gln Gly Ile Ser Ser Trp Leu Ala
1               5                   10
```

<210> SEQ ID NO 31
<211> LENGTH: 12
<212> TYPE: PRT
<213> ORGANISM: Homo sapiens

<400> SEQUENCE: 31

```
Arg Ala Ser Gln Ser Val Ser Ser Ser Phe Leu Ala
1               5                   10
```

<210> SEQ ID NO 32
<211> LENGTH: 7
<212> TYPE: PRT
<213> ORGANISM: Homo sapiens

<400> SEQUENCE: 32

```
Asp Ala Ser Ser Leu Glu Ser
1               5
```

<210> SEQ ID NO 33
<211> LENGTH: 7
<212> TYPE: PRT
<213> ORGANISM: Homo sapiens

<400> SEQUENCE: 33

```
Asp Ala Ser Asn Arg Ala Thr
1               5
```

<210> SEQ ID NO 34
<211> LENGTH: 7
<212> TYPE: PRT
<213> ORGANISM: Homo sapiens

<400> SEQUENCE: 34

```
Asp Ala Ser Asn Leu Glu Arg
1               5
```

<210> SEQ ID NO 35
<211> LENGTH: 7
<212> TYPE: PRT
<213> ORGANISM: Homo sapiens

<400> SEQUENCE: 35

```
Gly Ala Ser Ser Leu Gln Ser
1               5
```

<210> SEQ ID NO 36
<211> LENGTH: 7
<212> TYPE: PRT
<213> ORGANISM: Homo sapiens

<400> SEQUENCE: 36

```
Gly Ala Ser Ser Arg Ala Thr
1               5
```

```
<210> SEQ ID NO 37
<211> LENGTH: 9
<212> TYPE: PRT
<213> ORGANISM: Homo sapiens

<400> SEQUENCE: 37

Gln Gln Phe Asn Ser Tyr Pro Leu Thr
1               5

<210> SEQ ID NO 38
<211> LENGTH: 9
<212> TYPE: PRT
<213> ORGANISM: Homo sapiens

<400> SEQUENCE: 38

Gln Gln Arg Ser Asn Trp Pro Leu Thr
1               5

<210> SEQ ID NO 39
<211> LENGTH: 9
<212> TYPE: PRT
<213> ORGANISM: Homo sapiens

<400> SEQUENCE: 39

Gln Gln Phe Asn Ser Phe Pro Leu Thr
1               5

<210> SEQ ID NO 40
<211> LENGTH: 9
<212> TYPE: PRT
<213> ORGANISM: Homo sapiens

<400> SEQUENCE: 40

Gln Gln Tyr Asn Ser Tyr Pro Arg Thr
1               5

<210> SEQ ID NO 41
<211> LENGTH: 9
<212> TYPE: PRT
<213> ORGANISM: Homo sapiens

<400> SEQUENCE: 41

Gln Gln Tyr Gly Ser Ser Pro Leu Thr
1               5

<210> SEQ ID NO 42
<211> LENGTH: 107
<212> TYPE: PRT
<213> ORGANISM: Homo sapiens

<400> SEQUENCE: 42

Val Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Arg Ala
            20                  25                  30

Leu Ala Trp Tyr Gln Gln Lys Pro Gly Lys Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
```

```
                85                  90                  95

Thr Phe Gly Gly Gly Thr Lys Val Glu Ile Lys
            100                 105

<210> SEQ ID NO 43
<211> LENGTH: 107
<212> TYPE: PRT
<213> ORGANISM: Homo sapiens

<400> SEQUENCE: 43

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 44
<211> LENGTH: 107
<212> TYPE: PRT
<213> ORGANISM: Homo sapiens

<400> SEQUENCE: 44

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Arg Ala
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Phe Pro Leu
                85                  90                  95

Thr Phe Gly Gly Gly Thr Lys Val Glu Ile Lys
            100                 105

<210> SEQ ID NO 45
<211> LENGTH: 107
<212> TYPE: PRT
<213> ORGANISM: Homo sapiens

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45
```

```
Tyr Gly Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Arg
                 85                  90                  95

Thr Phe Gly Gln Gly Thr Lys Val Glu Ile Lys
                100                 105

<210> SEQ ID NO 46
<211> LENGTH: 108
<212> TYPE: PRT
<213> ORGANISM: Homo sapiens

<400> SEQUENCE: 46

Glu Ile Val Leu Thr Gln Ser Pro Gly Thr Leu Ser Leu Ser Pro Gly
 1               5                  10                  15

Asp Arg Ala Thr Leu Ser Cys Arg Ala Ser Gln Ser Val Ser Ser Ser
                20                  25                  30

Phe Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Leu Thr Phe Gly Gly Gly Thr Lys Val Glu Ile Lys
                100                 105

<210> SEQ ID NO 47
<211> LENGTH: 463
<212> TYPE: PRT
<213> ORGANISM: Homo sapiens

<400> SEQUENCE: 47

Met Glu Phe Gly Leu Asn Trp Val Phe Leu Val Ala Leu Leu Arg Asp
 1               5                  10                  15

Val Gln Cys Gln Val Gln Leu Val Glu Ser Gly Gly Gly Val Val Gln
                20                  25                  30

Pro Gly Arg Ser Leu Arg Leu Ser Cys Ala Ala Ser Gly Phe Thr Phe
             35                  40                  45

Phe Ser Tyr Ala Met His Trp Val Arg Gln Thr Pro Gly Lys Gly Leu
         50                  55                  60

Glu Trp Val Ala Val Ile Trp Phe Asp Gly Ser Asn Glu Asn Tyr Val
 65                  70                  75                  80

Asp Ser Val Lys Gly Arg Phe Thr Ile Ser Arg Asp Asn Ser Lys Asn
                 85                  90                  95

Thr Leu Tyr Leu Gln Met Asn Thr Leu Arg Ala Glu Asp Thr Ala Val
                100                 105                 110

Tyr Tyr Cys Ala Arg Asp Ala Trp Ser Tyr Phe Asp Tyr Trp Gly Gln
            115                 120                 125

Gly Thr Leu Val Thr Val Ser Ser Ala Ser Thr Lys Gly Pro Ser Val
        130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
```

-continued

```
                165                 170                 175
Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
            195                 200                 205

Ser Ser Ser Leu Gly Thr Lys Thr Tyr Thr Cys Asn Val Asp His Lys
            210                 215                 220

Pro Ser Asn Thr Lys Val Asp Lys Arg Val Glu Ser Lys Tyr Gly Pro
225                 230                 235                 240

Pro Cys Pro Pro Cys Pro Ala Pro Glu Phe Ala Gly Gly Pro Ser Val
                245                 250                 255

Phe Leu Phe Pro Pro Lys Pro Lys Asp Thr Leu Met Ile Ser Arg Thr
                260                 265                 270

Pro Glu Val Thr Cys Val Val Val Asp Val Ser Gln Glu Asp Pro Glu
            275                 280                 285

Val Gln Phe Asn Trp Tyr Val Asp Gly Val Glu Val His Asn Ala Lys
            290                 295                 300

Thr Lys Pro Arg Glu Glu Gln Phe Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Gly Leu Pro Ser Ser Ile Glu Lys Thr Ile
                340                 345                 350

Ser Lys Ala Lys Gly Gln Pro Arg Glu Pro Gln Val Tyr Thr Leu Pro
            355                 360                 365

Pro Ser Gln Glu Glu Met Thr Lys Asn Gln Val Ser Leu Thr Cys Leu
370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Arg Leu Thr Val Asp Lys Ser Arg
            420                 425                 430

Trp Gln Glu Gly Asn Val Phe Ser Cys Ser Val Met His Glu Ala Leu
            435                 440                 445

His Asn His Tyr Thr Gln Lys Ser Leu Ser Leu Ser Leu Gly Lys
            450                 455                 460

<210> SEQ ID NO 48
<211> LENGTH: 236
<212> TYPE: PRT
<213> ORGANISM: Homo sapiens

<400> SEQUENCE: 48

Met Asp Met Arg Val Pro Ala Gln Leu Leu Gly Leu Leu Leu Leu Trp
1               5                   10                  15

Leu Pro Gly Ala Arg Cys Val Ile Gln Leu Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Ser Arg Ala Leu Ala Trp Tyr Gln Gln Lys Pro Gly Lys
    50                  55                  60

Gly Pro Lys Leu Leu Ile Tyr Asp Ala Ser Ser Leu Glu Ser Gly Val
65                  70                  75                  80

Pro Ser Arg Phe Ser Gly Ser Gly Ser Gly Thr Asp Phe Thr Leu Thr
```

|   |   | 85 |   |   | 90 |   |   | 95 |   |   |   |
|---|---|---|---|---|---|---|---|---|---|---|---|

Ile Ser Ser Leu Gln Pro Glu Asp Phe Ala Thr Tyr Tyr Cys Gln Gln
                                100                 105                 110

Phe Asn Ser Tyr Pro Leu Thr Phe Gly Gly Gly Thr Lys Val Glu Ile
            115                 120                 125

Lys Arg Thr Val Ala Ala Pro Ser Val Phe Ile Phe Pro Pro Ser Asp
        130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 49
<211> LENGTH: 15
<212> TYPE: DNA
<213> ORGANISM: Homo sapiens

<400> SEQUENCE: 49
agctatgcca tgcac                                                    15

<210> SEQ ID NO 50
<211> LENGTH: 15
<212> TYPE: DNA
<213> ORGANISM: Homo sapiens

<400> SEQUENCE: 50
aactattgga tgagc                                                    15

<210> SEQ ID NO 51
<211> LENGTH: 15
<212> TYPE: DNA
<213> ORGANISM: Homo sapiens

<400> SEQUENCE: 51
agctatgcca tgcac                                                    15

<210> SEQ ID NO 52
<211> LENGTH: 15
<212> TYPE: DNA
<213> ORGANISM: Homo sapiens

<400> SEQUENCE: 52
cggtctggca tacac                                                    15

<210> SEQ ID NO 53
<211> LENGTH: 15
<212> TYPE: DNA
<213> ORGANISM: Homo sapiens

<400> SEQUENCE: 53
agctatggaa tgcac                                                    15

```
<210> SEQ ID NO 54
<211> LENGTH: 51
<212> TYPE: DNA
<213> ORGANISM: Homo sapiens

<400> SEQUENCE: 54
gttatatggt ttgatggaag taatgaaaac tatgtagact ccgtgaaggg c          51

<210> SEQ ID NO 55
<211> LENGTH: 51
<212> TYPE: DNA
<213> ORGANISM: Homo sapiens

<400> SEQUENCE: 55
aacataaagc aagatggaag tgagaagtac tatgtggact ctgtgagggg c          51

<210> SEQ ID NO 56
<211> LENGTH: 51
<212> TYPE: DNA
<213> ORGANISM: Homo sapiens

<400> SEQUENCE: 56
gttttatggt ttgatggaag taatgaagac tatgcagact ccgtgaaggg c          51

<210> SEQ ID NO 57
<211> LENGTH: 51
<212> TYPE: DNA
<213> ORGANISM: Homo sapiens

<400> SEQUENCE: 57
gttatatggt atgatggaat ttataagtac tatgcagact ccgtgaaggg c          51

<210> SEQ ID NO 58
<211> LENGTH: 48
<212> TYPE: DNA
<213> ORGANISM: Homo sapiens

<400> SEQUENCE: 58
gctattggtg ttggtggtgg cacataccat gtagattccg tgaagggc              48

<210> SEQ ID NO 59
<211> LENGTH: 24
<212> TYPE: DNA
<213> ORGANISM: Homo sapiens

<400> SEQUENCE: 59
gatgcctgga gctactttga ctac                                        24

<210> SEQ ID NO 60
<211> LENGTH: 42
<212> TYPE: DNA
<213> ORGANISM: Homo sapiens

<400> SEQUENCE: 60
gattactttg gttcggggac ttatttcttc tactttgact ac                    42

<210> SEQ ID NO 61
<211> LENGTH: 24
<212> TYPE: DNA
<213> ORGANISM: Homo sapiens

<400> SEQUENCE: 61
gatggctggg gatactttga ctac                                        24
```

```
<210> SEQ ID NO 62
<211> LENGTH: 24
<212> TYPE: DNA
<213> ORGANISM: Homo sapiens

<400> SEQUENCE: 62
gagaagaact ggggaattga ctac                                            24

<210> SEQ ID NO 63
<211> LENGTH: 33
<212> TYPE: DNA
<213> ORGANISM: Homo sapiens

<400> SEQUENCE: 63
gatcctgggt tcggggaggt ctactttgac tat                                  33

<210> SEQ ID NO 64
<211> LENGTH: 351
<212> TYPE: DNA
<213> ORGANISM: Homo sapiens

<400> SEQUENCE: 64
caggtgcaac tggtggagtc tgggggaggc gtggtccagc ctggggaggtc cctgagactc    60 tcctgtgcag cgtctggatt caccttcttt agctatgcca tgcactgggt ccgccagact   120
ccaggcaagg ggctggagtg ggtggcagtt atatggtttg atggaagtaa tgaaaactat   180
gtagactccg tgaagggccg attcaccatc tccagagaca attccaagaa cacgctgtat   240
ctgcaaatga cacccctgag agccgaggac acggctgtgt attactgtgc gagagatgcc   300
tggagctact ttgactactg gggccaggga accctggtca ccgtctcctc a            351

<210> SEQ ID NO 65
<211> LENGTH: 369
<212> TYPE: DNA
<213> ORGANISM: Homo sapiens

<400> SEQUENCE: 65
gaggtgcagc tggtggagtc tgggggaggc ttggtccagc ctgggggtc cctgagactc     60 tcctgtgcag cctctggatt cattttcagt aactattgga tgagctgggt ccgccaggct   120
ccagggaaag ggctggagtg ggtggccaac ataaagcaag atggaagtga aagtactat    180 gtggactctg tgaggggccg attcaccgtc tccagagaca cgccaagaa ctcactgtat    240 ctgcaaatga cagcctgag agccgaggac acggctgtgt attactgtgc gagggattac   300
tttggttcgg ggacttattt cttctacttt gactactggg gccagggaac cctggtcacc  360
ttctcctca                                                          369

<210> SEQ ID NO 66
<211> LENGTH: 351
<212> TYPE: DNA
<213> ORGANISM: Homo sapiens

<400> SEQUENCE: 66
caggtgcagc tggtggagtc tgggggaggc gtggtccagc ctggggaggtc cctgagactc    60 tcctgtgcag cgtctggatt caccttcagt agctatgcca tgcactgggt ccgccaggct   120
ccaggcaagg ggctggagtg ggtggcagtt ttatggtttg atggaagtaa tgaagactat   180
gcagactccg tgaagggccg attcaccatc tccagagaca actccaagaa cacgctgtat   240
ctgcaaatga cagcctgag agccgaggac acggctgtgt attactgtgc gagagatggc   300
tggggatact ttgactactg gggccaggga accctggtca ccgtctcctc a            351
```

<210> SEQ ID NO 67
<211> LENGTH: 351
<212> TYPE: DNA
<213> ORGANISM: Homo sapiens

<400> SEQUENCE: 67

```
caggtgcagc tggtggactc tgggggagac gtggtccagc ctggggaggtc cctgagactc      60
tcctgtgcag cgtctggatt cagtttcagt cggtctggca tacactgggt ccgccaggct     120
ccaggcaagg ggctggagtg ggtggcagtt atatggtatg atggaattta taagtactat     180
gcagactccg tgaagggccg attcaccatc tccagagaca attccaagaa cacgctgtat     240
ctgcaaatga acagcctgag ggccgaggac acggctgtgt attactgtgc gagagagaag     300
aactggggaa ttgactactg gggccaggga accctggtca ccgtctcctc a              351
```

<210> SEQ ID NO 68
<211> LENGTH: 357
<212> TYPE: DNA
<213> ORGANISM: Homo sapiens

<400> SEQUENCE: 68

```
gaggttcagc tggtgcagtc tggggaggc ttggtacatc cggggggtc cctgagactc        60
tcctgtgcag gctctggatt ccccgtcagt agctatggaa tgcactgggt tcgccaggct     120
ccaggaaaag gtctggagtg ggtatcagct attggtgttg gtggtggcac ataccatgta     180
gattccgtga aggccgatt caccatctcc agagacaatg ccaagaactc cttgtatctt      240
caaatgaaca gcctgagagc cggggacatg gctgtgtatt actgtgcaag agatcctggg     300
ttcggggagg tctactttga ctattggggc caggaaccc tggtcaccgt ctcctca         357
```

<210> SEQ ID NO 69
<211> LENGTH: 33
<212> TYPE: DNA
<213> ORGANISM: Homo sapiens

<400> SEQUENCE: 69

```
cgggcaagtc agggcattag cagggcttta gcc                                    33
```

<210> SEQ ID NO 70
<211> LENGTH: 33
<212> TYPE: DNA
<213> ORGANISM: Homo sapiens

<400> SEQUENCE: 70

```
agggccagtc agagtgttag cagctactta gcc                                    33
```

<210> SEQ ID NO 71
<211> LENGTH: 33
<212> TYPE: DNA
<213> ORGANISM: Homo sapiens

<400> SEQUENCE: 71

```
cgggcaagtc agggcattag cagagcttta gcc                                    33
```

<210> SEQ ID NO 72
<211> LENGTH: 33
<212> TYPE: DNA
<213> ORGANISM: Homo sapiens

<400> SEQUENCE: 72

```
cgggcgagtc agggtattag cagctggtta gcc                                    33
```

```
<210> SEQ ID NO 73
<211> LENGTH: 36
<212> TYPE: DNA
<213> ORGANISM: Homo sapiens

<400> SEQUENCE: 73
agggccagtc agagtgttag cagcagcttc ttagcc                         36

<210> SEQ ID NO 74
<211> LENGTH: 21
<212> TYPE: DNA
<213> ORGANISM: Homo sapiens

<400> SEQUENCE: 74
gatgcctcca gtttggaaag t                                         21

<210> SEQ ID NO 75
<211> LENGTH: 21
<212> TYPE: DNA
<213> ORGANISM: Homo sapiens

<400> SEQUENCE: 75
gatgcatcca acagggccac t                                         21

<210> SEQ ID NO 76
<211> LENGTH: 21
<212> TYPE: DNA
<213> ORGANISM: Homo sapiens

<400> SEQUENCE: 76
gatgcctcca atttggaaag a                                         21

<210> SEQ ID NO 77
<211> LENGTH: 21
<212> TYPE: DNA
<213> ORGANISM: Homo sapiens

<400> SEQUENCE: 77
ggtgcatcca gtttgcaaag t                                         21

<210> SEQ ID NO 78
<211> LENGTH: 21
<212> TYPE: DNA
<213> ORGANISM: Homo sapiens

<400> SEQUENCE: 78
ggtgcatcca gcagggccac t                                         21

<210> SEQ ID NO 79
<211> LENGTH: 27
<212> TYPE: DNA
<213> ORGANISM: Homo sapiens

<400> SEQUENCE: 79
caacagttta atagttaccc tctcact                                   27

<210> SEQ ID NO 80
<211> LENGTH: 27
<212> TYPE: DNA
<213> ORGANISM: Homo sapiens

<400> SEQUENCE: 80
cagcagcgta gcaactggcc gctcact                                   27
```

<210> SEQ ID NO 81
<211> LENGTH: 27
<212> TYPE: DNA
<213> ORGANISM: Homo sapiens

<400> SEQUENCE: 81
caacagttta atagtttccc gctcact                                27

<210> SEQ ID NO 82
<211> LENGTH: 27
<212> TYPE: DNA
<213> ORGANISM: Homo sapiens

<400> SEQUENCE: 82
caacagtata atagttaccc tcggacg                                27

<210> SEQ ID NO 83
<211> LENGTH: 27
<212> TYPE: DNA
<213> ORGANISM: Homo sapiens

<400> SEQUENCE: 83
cagcagtatg gtagctcacc gctcact                                27

<210> SEQ ID NO 84
<211> LENGTH: 321
<212> TYPE: DNA
<213> ORGANISM: Homo sapiens

<400> SEQUENCE: 84
gtcatccagt tgacccagtc tccatcctcc ctgtctgcat ctgtaggaga cagagtcacc    60
atcacttgcc gggcaagtca gggcattagc agggctttag cctggtatca gcagaaacca   120
gggaaaggtc ctaagctcct gatctatgat gcctccagtt tggaaagtgg ggtcccatca   180
aggttcagcg gcagtggatc tgggacagat ttcactctca ccatcagcag cctgcagcct   240
gaagattttg caacttatta ctgtcaacag tttaatagtt accctctcac tttcggcgga   300
gggaccaagg tggagatcaa a                                            321

<210> SEQ ID NO 85
<211> LENGTH: 321
<212> TYPE: DNA
<213> ORGANISM: Homo sapiens

<400> SEQUENCE: 85
gaaattgtgt tgacacagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtagcaact ggccgctcac tttcggcgga   300
gggaccaagg tggagatcaa a                                            321

<210> SEQ ID NO 86
<211> LENGTH: 321
<212> TYPE: DNA
<213> ORGANISM: Homo sapiens

<400> SEQUENCE: 86
gccatccagt tgacccagtc tccatcctcc ctgtctgcat ctgtaggaga cagagtcacc    60

| | |
|---|---|
| atcacttgcc gggcaagtca gggcattagc agagctttag cctggtatca gcagaaacca | 120 |
| gggaaagctc ctaagctcct gatctatgat gcctccaatt tggaaagagg ggtcccatca | 180 |
| aggttcagcg gcagtggatc tgggacagat ttcactctca ccatcagcag cctgcaacct | 240 |
| gaggattttg caacttatta ctgtcaacag tttaatagtt tcccgctcac tttcggcgga | 300 |
| gggaccaagg tggagatcaa a | 321 |

<210> SEQ ID NO 87
<211> LENGTH: 321
<212> TYPE: DNA
<213> ORGANISM: Homo sapiens

<400> SEQUENCE: 87

| | |
|---|---|
| gacatccaga tgacccagtc tccatcctca ctgtctgcat ctgtaggaga cagagtcacc | 60 |
| atcacttgtc gggcgagtca gggtattagc agctggttag cctggtatca gcagaaacca | 120 |
| gagaaagccc ctaagtccct gatctatggt gcatccagtt tgcaaagtgg ggtcccatca | 180 |
| aggttcagcg gcagtggatc tgggacagat ttcactctca ccatcagcag cctgcagcct | 240 |
| gaagattttg caacttatta ctgccaacag tataatagtt accctcggac gttcggccaa | 300 |
| gggaccaagg tggaaatcaa a | 321 |

<210> SEQ ID NO 88
<211> LENGTH: 324
<212> TYPE: DNA
<213> ORGANISM: Homo sapiens

<400> SEQUENCE: 88

| | |
|---|---|
| gaaattgtgt tgacgcagtc tccaggcacc ctgtctttgt ctccagggga tagagccacc | 60 |
| ctctcctgca gggccagtca gagtgttagc agcagcttct tagcctggta ccagcagaaa | 120 |
| cctggccagg ctcccaggct cctcatctat ggtgcatcca gcagggccac tggcatccca | 180 |
| gacaggttca gtggcagtgg gtctgggaca gacttcactc tcaccatcag cagactggag | 240 |
| cctgaagatt ttgcagtgta ttactgtcag cagtatggta gctcaccgct cactttcggc | 300 |
| ggagggacca aggtggagat caaa | 324 |

<210> SEQ ID NO 89
<211> LENGTH: 1392
<212> TYPE: DNA
<213> ORGANISM: Homo sapiens

<400> SEQUENCE: 89

| | |
|---|---|
| atggagtttg gctgaactg gttttcctc gttgctcttt taagagatgt ccagtgtcag | 60 |
| gtgcaactgg tggagtctgg gggaggcgtg gtccagcctg gaggtccct gagactctcc | 120 |
| tgtgcagcgt ctggattcac cttctttagc tatgccatgc actgggtccg ccagactcca | 180 |
| ggcaagggc tggagtgggt ggcagttata tggtttgatg gaagtaatga aaactatgta | 240 |
| gactccgtga agggccgatt caccatctcc agagacaatt ccaagaacac gctgtatctg | 300 |
| caaatgaaca ccctgagagc cgaggacacg gctgtgtatt actgtgcgag agatgcctgg | 360 |
| agctactttg actactgggg ccagggaacc ctggtcaccg tctcctcagc tagcaccaag | 420 |
| ggcccatccg tcttccccct ggcgccctgc tccaggagca cctccgagag cacagccgcc | 480 |
| ctgggctgcc tggtcaagga ctacttcccc gaaccggtga cggtgtcgtg gaactcaggc | 540 |
| gccctgacca gcggcgtgca caccttcccg gctgtcctac agtcctcagg actctactcc | 600 |
| ctcagcagcg tggtgaccgt gccctccagc agcttgggca cgaagaccta cacctgcaac | 660 |

```
gtagatcaca agcccagcaa caccaaggtg gacaagagag ttgagtccaa atatggtccc      720
ccatgcccac catgcccagc acctgagttc gcggggggac catcagtctt cctgttcccc      780
ccaaaaccca aggacactct catgatctcc cggacccctg aggtcacgtg cgtggtggtg      840
gacgtgagcc aggaagaccc cgaggtccag ttcaactggt acgtggatgg cgtggaggtg      900
cataatgcca agacaaagcc gcgggaggag cagttcaaca gcacgtaccg tgtggtcagc      960
gtcctcaccg tcctgcacca ggactggctg aacggcaagg agtacaagtg caaggtctcc     1020
aacaaaggcc tcccgtcctc catcgagaaa accatctcca aagccaaagg gcagccccga     1080
gagccacagg tgtacaccct gcccccatcc caggaggaga tgaccaagaa ccaggtcagc     1140
ctgacctgcc tggtcaaagg cttctacccc agcgacatcg ccgtggagtg ggagagcaat     1200
gggcagccgg agaacaacta caagaccacg cctcccgtgc tggactccga cggctccttc     1260
ttcctctaca gcaggctaac cgtggacaag agcaggtggc aggaggggaa tgtcttctca     1320
tgctccgtga tgcatgaggc tctgcacaac cactacacac agaagagcct ctccctgtct     1380
ctgggtaaat ga                                                         1392

<210> SEQ ID NO 90
<211> LENGTH: 711
<212> TYPE: DNA
<213> ORGANISM: Homo sapiens

<400> SEQUENCE: 90
atggacatga gggtccccgc tcagctcctg gggcttctgc tgctctggct cccaggtgcc       60
agatgtgtca tccagttgac ccagtctcca tcctccctgt ctgcatctgt aggagacaga      120
gtcaccatca cttgccgggc aagtcagggc attagcaggg ctttagcctg gtatcagcag      180
aaaccaggga aagtcctaa gctcctgatc tatgatgcct ccagtttgga aagtggggtc      240
ccatcaaggt tcagcggcag tggatctggg acagatttca ctctcaccat cagcagcctg      300
cagcctgaag attttgcaac ttattactgt caacagttta atagttaccc tctcactttc      360
ggcggaggga ccaaggtgga gatcaaacgt acggtggctg caccatctgt cttcatcttc      420
ccgccatctg atgagcagtt gaaatctgga actgcctctg ttgtgtgcct gctgaataac      480
ttctatccca gagaggccaa agtacagtgg aaggtggata acgccctcca atcgggtaac      540
tcccaggaga gtgtcacaga gcaggacagc aaggacagca cctacagcct cagcagcacc      600
ctgacgctga gcaaagcaga ctacgagaaa cacaaagtct acgcctgcga agtcacccat      660
cagggcctga gctcgcccgt cacaaagagc ttcaacaggg gagagtgtta g              711
```

METHODS OF TREATING AN INFLAMMATORY CONDITION INVOLVING VAP-1-MEDIATED ADHESION WITH VAP-1-SPECIFIC ANTIBODIES

CROSS-REFERENCE TO RELATED APPLICATIONS

The present application is a Division of U.S. application Ser. No. 12/081,707 filed on Apr. 18, 2008 now U.S. Pat. No. 7,897,149. Application Ser. No. 12/081,707 claims the benefit of priority U.S. Provisional Appl. No. 60/907,904, filed Apr. 20, 2007. Application Ser. No. 12/081,707 also claims the benefit of foreign priority under 35 U.S.C. §119 of Finland Appl. No. 20075278, filed Apr. 20, 2007. The content of the aforesaid applications are incorporated by reference in their entirety.

FIELD OF THE INVENTION

The present invention relates to nucleic acid sequences encoding fully human monoclonal antibodies recognizing a human endothelial cell adhesion protein, VAP-1, and particularly to a fully human monoclonal antibody, designated BTT-1023, which recognizes a functional epitope of VAP1.

BACKGROUND OF THE INVENTION

The publications and other material used herein to illuminate the background of the invention, and in particular, cases to provide additional details respecting the practice, are incorporated by reference.

Generally, whole antibodies share a common Y-shape structure composed of two identical light chains and two identical heavy chains. These four polypeptide subunits are assembled so that the two heavy chains are linked, and a light chain is attached to each heavy chain by disulfide bonds. Each polypeptide constituting the antibody consists of a variable and a constant region.

The variable region is located in the arms of the Y-shaped antibody, and determines the antigen-binding specificity of the antibody. This region contains short amino acid sequences, which are responsible for the binding of the antibody to its antigen. These regions are called complementarity determining regions (CDRs). The remaining parts of the variable regions are important for the conformation of the antigen-binding pocket as a whole.

The constant region of an antibody is located at the base of the heavy chains, and determines the antibody's ability to activate immune reactions through interactions with specific receptors. These regions are generally highly conserved, and variability is limited to five basic isoforms, IgA, IgD, IgE, IgG and IgM.

Vascular adhesion protein-1 (VAP-1) is a non-classical, inflammation-inducible, adhesion molecule expressed on vascular endothelial cells, where it mediates leukocyte rolling under physiological shear. In this role it contributes towards lymphocyte re-circulation through high endothelial venules (HEV's) of secondary lymphoid tissue as part of the normal process of immune surveillance.

However, under inflammatory conditions, VAP-1 promotes the infiltration of leukocytes into inflamed tissue, thereby contributing to and maintaining the inflammatory response. This infiltration can in itself be damaging in chronic inflammatory diseases such as rheumatoid arthritis, inflammatory bowel disease, psoriasis and many autoimmune and other inflammatory diseases. In other settings, the massive infiltration of pro-inflammatory cells into tissue after the severe tissue damage resulting from myocardial infarction, stroke and other diseases contributes to the tissue destruction seen in these acute inflammatory responses. Reducing the infiltration of cells into sites of inflammation by preventing VAP-1 function with blocking antibodies is likely to allow the inflammation to resolve and lead to an improvement in the clinical symptoms of these diseases.

U.S. Pat. No. 5,580,780 describes a monoclonal antibody (mAb), 1B2, which recognizes VAP-1 and which can block lymphocyte binding to tonsillar HEV in a frozen section assay. MAb 1B2 is a murine IgM-antibody and is specific for VAP-1.

The use of murine mAbs as therapeutics has a limited potential, since the human immune system recognizes murine antibodies as foreign material and produces human anti-mouse antibodies (HAMA) to clear them from the body. This immune reaction is a major limitation to the use of murine antibodies in long-term therapy when repeated administration is needed. The use of murine anti-VAP-1 antibodies in the clinic might have to be limited to patients treated with immunosuppressants, and thus less prone to HAMA reactions, and to treatment regimens, where once only administration of the antibodies is feasible, such as in ischaemia reperfusion injury in acute infarction or acute respiratory distress syndrome.

One further disadvantage related to the use of murine IgM anti-VAP-1 antibodies in therapy is the unfavorable kinetic profile of such antibodies, i.e., the short half-life, which render them unsuitable for use in chronic disorders, such as rheumatoid arthritis, inflammatory bowel disease, psoriasis and many other diseases.

Several methods of creating less immunogenic monoclonal antibodies are known in the art. Some approaches include "humanizing" the antibodies. Frequently used strategies are to create chimeric mAbs, humanized mAbs or fully human mAbs. Chimeric mAbs are antibodies wherein the variable region is murine derived whereas the constant region is of human origin. In chimeric antibodies, approximately 70% of the rodent antibody molecule is usually replaced with the corresponding human sequences whilst maintaining the rodent antigen-binding sites with their particular specificities and affinities. Humanized antibodies are antibodies wherein the variable region may be murine derived but which has been mutated so as to more resemble a human antibody and may contain a constant region of human origin. Fully human antibodies are antibodies wherein both the variable region and the constant region are of human origin.

International patent publication WO03/093319 discloses a chimeric anti-VAP-1 monoclonal antibody BTT-1002, which has the potential to have reduced immunogenicity compared to the corresponding murine antibodies.

However, being a chimeric antibody, BTT-1002 still has protein sequences corresponding to the variable regions of the antibody that are derived directly and without modification from the original mouse antibody. This antibody may still be recognized as foreign and be immunogenic when administered to man. Its pharmacological properties, such as its elimination half life and functional properties, may also be compromised due to its immunogenicity and the resulting production of antibodies against it.

Thus, there is a need in the art for a fully human anti-VAP-1 antibody with reduced immunogenicity and improved pharmacological properties.

BRIEF DESCRIPTION OF THE INVENTION

The present invention is broadly directed to novel fully human anti-VAP-1 antibodies, methods of producing such antibodies and uses of the antibodies. The present invention is further directed to polynucleotides encoding said anti-VAP-1 antibodies.

An object of the present invention is to provide a fully human monoclonal antibody for use in in vivo diagnostics and/or therapy, which has a reduced potential to elicit an immune response in the patients and which has a favorable pharmacological profile for therapeutic purposes.

Another object of the present invention is to provide heavy and light chains of fully human anti-VAP-1 antibodies, or fragments thereof.

A further object of the present invention is to provide nucleic acids encoding fully human anti-VAP-1 antibodies, or fragments thereof, as well as expression vectors and host cells incorporating these nucleic acids for the recombinant expression of anti-VAP-1 antibodies.

Another embodiment of the present invention is directed to methods for producing the fully human anti-VAP-1 antibodies according to the present embodiments by recombinant production methods.

Pharmaceutical compositions comprising said antibodies and therapeutic uses thereof are also disclosed.

BRIEF DESCRIPTION OF THE FIGURES

In the following the invention will be described in greater detail by means of embodiments with reference to the attached figures, in which FIGS. 1 to 5 show the nucleotide sequences and the corresponding amino acid sequences of the variable regions of anti-VAP-1 antibodies 8C10 (FIGS. 1A and 1B), 8A4 (FIGS. 2A and 2B), 3F10 (FIGS. 3A and 3B), 5F12 (FIGS. 4A and 4B), and 4B3 (FIGS. 5A and 5B). Amino acid sequences of the variable light ($V_L$) chain (A) and variable heavy ($V_H$) chain (B) were deduced from the cloned cDNAs. The three CDRs in each amino acid chain are shown in bold with the corresponding nucleotide sequences underlined.

Figure 7:
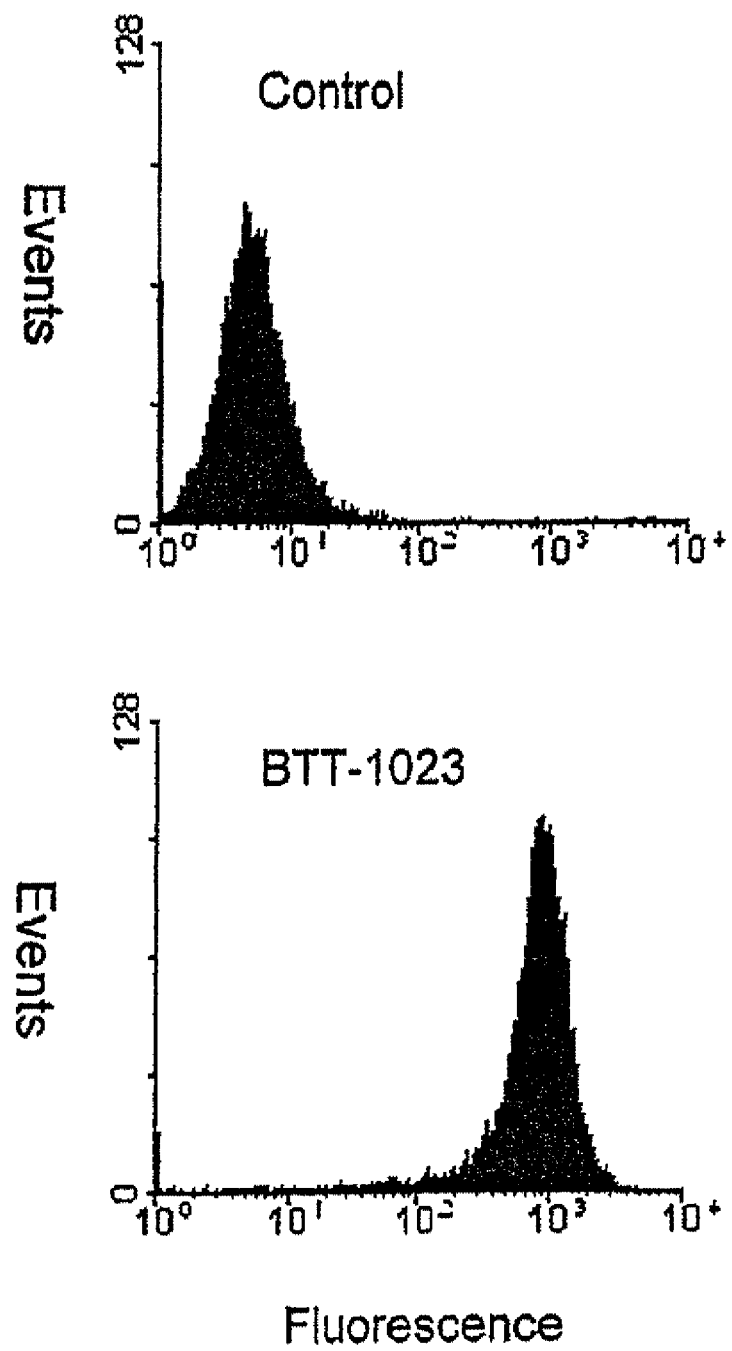

In particular, the amino acid sequence shown in FIG. 1A corresponds to SEQ ID NO: 42, whereas the nucleotide sequence corresponds to SEQ ID NO: 84. The three CDRs in the amino acid sequence are shown in bold and correspond to SEQ ID NOS: 27, 32, and 37, respectively. The corresponding nucleotide sequences are underlined and correspond to SEQ ID NOS: 69, 74, and 79, respectively.

The amino acid sequence shown in FIG. 1B corresponds to SEQ ID NO: 19, whereas the nucleotide sequence corresponds to SEQ ID NO: 64. The three CDRs in the amino acid sequence are shown in bold and correspond to SEQ ID NOS: 4, 9, and 14 respectively. The corresponding nucleotide sequences are underlined and correspond to SEQ ID NOS: 49, 54, and 59, respectively.

The amino acid sequence shown in FIG. 2A corresponds to SEQ ID NO: 43, whereas the nucleotide sequence corresponds to SEQ ID NO: 85. The three CDRs in the amino acid sequence are shown in bold and correspond to SEQ ID NOS: 28, 33, and 38 respectively. The corresponding nucleotide sequences are underlined and correspond to SEQ ID NOS: 70, 75, and 80, respectively.

The amino acid sequence shown in FIG. 2B corresponds to SEQ ID NO: 20, whereas the nucleotide sequence corresponds to SEQ ID NO: 65. The three CDRs in the amino acid sequence are shown in bold and correspond to SEQ ID NOS: 5, 10, and 15, respectively. The corresponding nucleotide sequences are underlined and correspond to SEQ ID NOS: 50, 55, and 60, respectively.

The amino acid sequence shown in FIG. 3A corresponds to SEQ ID NO: 44, whereas the nucleotide sequence corresponds to SEQ ID NO: 86. The three CDRs in the amino acid sequence are shown in bold and correspond to SEQ ID NOS: 29, 34, and 39 respectively. The corresponding nucleotide sequences are underlined and correspond to SEQ ID NOS: 71, 76, and 81, respectively.

The amino acid sequence shown in FIG. 3B corresponds to SEQ ID NO: 21, whereas the nucleotide sequence corresponds to SEQ ID NO: 66. The three CDRs in the amino acid sequence are shown in bold and correspond to SEQ ID NOS: 6, 11, and 16 respectively. The corresponding nucleotide sequences are underlined and correspond to SEQ ID NOS: 51, 56, and 61, respectively.

The amino acid sequence shown in FIG. 4A corresponds to SEQ ID NO: 45, whereas the nucleotide sequence corresponds to SEQ ID NO: 87. The three CDRs in the amino acid sequence are shown in bold and correspond to SEQ ID NOS: 30, 35, and 40 respectively. The corresponding nucleotide sequences are underlined and correspond to SEQ ID NOS: 72, 77, and 82, respectively.

The amino acid sequence shown in FIG. 4B corresponds to SEQ ID NO: 22, whereas the nucleotide sequence corresponds to SEQ ID NO: 67. The three CDRs in the amino acid sequence are shown in bold and correspond to SEQ ID NOS: 7, 12, and 17 respectively. The corresponding nucleotide sequences are underlined and correspond to SEQ ID NOS: 52, 57, and 62, respectively.

The amino acid sequence shown in FIG. 5A corresponds to SEQ ID NO: 46, whereas the nucleotide sequence corresponds to SEQ ID NO: 88. The three CDRs in the amino acid sequence are shown in bold and correspond to SEQ ID NOS: 31, 36, and 41 respectively. The corresponding nucleotide sequences are underlined and correspond to SEQ ID NOS: 73, 78, and 83, respectively.

The amino acid sequence shown in FIG. 5B corresponds to SEQ ID NO: 23, whereas the nucleotide sequence corresponds to SEQ ID NO: 68. The three CDRs in the amino acid sequence are shown in bold and correspond to SEQ ID NOS: 8, 13, and 18 respectively. The corresponding nucleotide sequences are underlined and correspond to SEQ ID NOS: 53, 58, and 63, respectively.

FIG. 6 shows an alignment of the protein sequence of the variable regions of the 8C10, 8A4, 3F10, 5F12, and 4B3 VH heavy chain showing the consensus sequence (FIG. 6A). An alignment of VH heavy chain CDR's 1 to 3 with a consensus sequence is shown in FIG. 6B, FIG. 6C and FIG. 6D. FIG. 6E shows an alignment of the protein sequence of the variable regions of the 8C10, 8A4, 3F10, 5F12, and 4B3 VL light chain showing the consensus sequence. An alignment of VL light chain CDR's 1 to 3 with a consensus sequence is shown in FIG. 6F, FIG. 6G and FIG. 6H.

In particular, FIG. 6A depicts the 8C10 $V_H$ sequence, which corresponds to SEQ ID NO: 19; the 8A4 $V_H$ sequence, which corresponds to SEQ ID NO: 20; the 3F10 $V_H$ sequence, which corresponds to SEQ ID NO: 21; the 5F12 $V_H$ sequence, which corresponds to SEQ ID NO: 22; and the 4B3 $V_H$ sequence, which corresponds to SEQ ID NO: 23. The consensus sequence is not included in the sequence listing.

FIG. 6B depicts the 8C10 $V_H$ sequence, which corresponds to SEQ ID NO: 4; the 8A4 $V_H$ sequence, which corresponds to SEQ ID NO: 5; the 3F10 $V_H$ sequence, which corresponds to SEQ ID NO: 6; the 5F12 $V_H$ sequence, which corresponds to SEQ ID NO: 7; the 4B3 $V_H$ sequence, which corresponds to SEQ ID NO: 8; and the consensus sequence, which corresponds to SEQ ID NO: 1.

FIG. 6C depicts the 8C10 $V_H$ sequence, which corresponds to SEQ ID NO: 9; the 8A4 $V_H$ sequence, which corresponds to SEQ ID NO: 10; the 3F10 $V_H$ sequence, which corresponds to SEQ ID NO: 11; the 5F12 V$_H$ sequence, which corresponds to SEQ ID NO: 12; the 4B3 V$_H$ sequence, which corresponds to SEQ ID NO: 13; and the consensus sequence, which corresponds to SEQ ID NO: 2.

FIG. 6D depicts the 8C10 V$_H$ sequence, which corresponds to SEQ ID NO: 14; the 8A4 V$_H$ sequence, which corresponds to SEQ ID NO: 15; the 3F10 V$_H$ sequence, which corresponds to SEQ ID NO: 16; the 5F12 V$_H$ sequence, which corresponds to SEQ ID NO: 17; the 4B3 V$_H$ sequence, which corresponds to SEQ ID NO: 18; and the consensus sequence, which corresponds to SEQ ID NO: 3.

FIG. 6E depicts the 8C10 V$_L$, sequence, which corresponds to SEQ ID NO: 42; the 8A4 V$_L$ sequence, which corresponds to SEQ ID NO: 43; the 3F10 V$_L$ sequence, which corresponds to SEQ ID NO: 44; the 5FI2 V$_L$ sequence, which corresponds to SEQ ID NO: 45; and the 4B3 V$_L$, sequence, which corresponds to SEQ ID NO: 46. The consensus sequence is not included in the sequence listing.

FIG. 6F depicts the 8C10 V$_L$ sequence, which corresponds to SEQ ID NO: 27; the 8A4 V$_L$ sequence, which corresponds to SEQ ID NO: 28; the 3F10 V$_L$ sequence, which corresponds to SEQ ID NO: 29; the 5F12 V$_L$ sequence, which corresponds to SEQ ID NO: 30; the 4B3 V$_L$ sequence, which corresponds to SEQ ID NO: 31; and the consensus sequence, which corresponds to SEQ ID NO 24.

FIG. 6G depicts the 8C10 V$_L$ sequence, which corresponds to SEQ ID NO: 32; the 8A4 V$_L$ sequence, which corresponds to SEQ ID NO: 33; the 3F10 V$_L$ sequence, which corresponds to SEQ ID NO: 34; the 5F12 V$_L$ sequence, which corresponds to SEQ ID NO: 35; the 4B3 V$_L$ sequence, which corresponds to SEQ ID NO: 36; and the consensus sequence, which corresponds to SEQ ID NO 25.

FIG. 6H depicts the 8C10 V$_L$ sequence, which corresponds to SEQ ID NO: 37; the 8A4 V$_L$ sequence, which corresponds to SEQ ID NO: 38; the 3F10 V$_L$ sequence, which corresponds to SEQ ID NO: 39; the 5F12 V$_L$ sequence, which corresponds to SEQ ID NO: 40; the 4B3 V$_L$ sequence, which corresponds to SEQ ID NO: 41; and the consensus sequence, which corresponds to SEQ ID NO 26.

FIG. 7 illustrates the VAP-1 binding of the recombinant fully human antibody r8C10 (BTT-1023) to Ax cells expressing human VAP-1 on the cell surface, demonstrated by FACS (fluorescence activated cell-sorting) analysis of BTT-1023 stained Ax VAP-1 cells compared to control stained cells.

Figure 8:
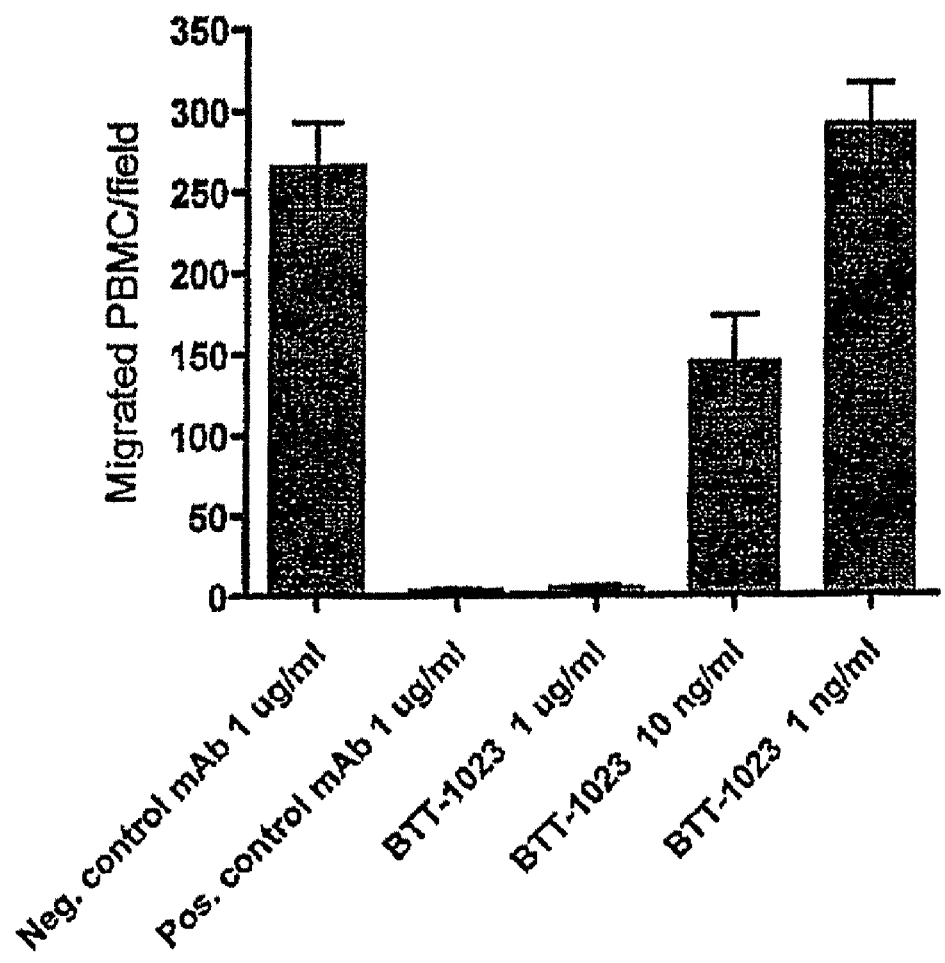

FIG. 8 illustrates the effect of BTT-1023 on leukocyte transmigration in vitro. The number of peripheral blood mononuclear cells (PBMC) transmigrated through endothelial cell monolayers treated with BTT1023 or control antibodies is shown. Error bars are standard error of the mean, N=6.

DETAILED DESCRIPTION OF THE INVENTION

The present invention is directed to fully human, such as recombinantly produced, monoclonal antibodies (mAbs) specifically recognizing human Vascular Adhesion Protein-1, VAP-1. The fully human monoclonal antibodies according to the present embodiments have reduced immunogenicity compared to corresponding humanized antibodies and are thus useful for treating a number of autoimmune diseases, inflammatory conditions and diseases of connective tissue, skin, and the gastrointestinal tract, central nervous system, and pulmonary systems, including conditions, such as chronic arthritis, inflammatory bowel diseases, and chronic dermatoses. The fully human VAP-1 antibodies are further useful for in vitro and in vivo diagnostic applications, including in vivo immunoscintigraphic imaging of inflammation sites.

The term "conservative sequence variant" as used herein, is intended to include nucleotide and amino acid sequence modifications, which do not significantly alter the binding properties of the fully human anti-VAP-1 antibodies according to the present embodiments. Conservative nucleotide sequence variants include variants arising from the degeneration of the genetic code and from silent mutations. Nucleotide substitutions, deletions and additions are also included. Conservative amino acid sequence variants include variants arising from amino acid substitutions with similar amino acids well known in the art. Amino acid deletions and additions are also included.

The polypeptides and polynucleotides according to the present embodiments include those, which have at least 80% sequence identity, or at least 85%, 90%, 95%, 96%, 97%, 98% or 99% sequence identity to the fully human anti-VAP-1 antibodies or to the polynucleotides encoding said antibodies described below.

The present invention provides a fully human anti-VAP-1 antibody heavy chain comprising at least one CDR consensus sequence selected form the group consisting of:

a) sequence $X_1X_2X_3X_4X_5$ (SEQ ID NO 1), wherein
$X_1$ is small polar or basic amino acid, such as S, N or R,
$X_2$ is aromatic or small polar amino acid, such as Y or S,
$X_3$ is small hydrophobic or aromatic amino acid, such as A, G or W,
$X_4$ is hydrophobic amino acid, such as M or I, and
$X_5$ is small polar or basic amino acid, such as H or S;

b) sequence $X_1X_2X_3X_4X_5G\ X_6X_7X_8X_9X_{10}X_{11}D\ S\ V\ X_{12}G$ (SEQ ID NO 2), wherein
$X_1$ is small amino acid, such as V, A or N,
$X_2$ is small aliphatic amino acid, such as I or L,
$X_3$ is aromatic, basic or hydrophobic amino acid, such as W, G or K,
$X_4$ is aromatic or aliphatic hydrophobic or polar amino acid, such as, F, Q, V or Y,
$X_5$ is small acidic or small amino acid, such as D or G,
$X_6$ is small or aliphatic amino acid, such as S, G or I,
$X_7$ is polar amino acid, such as N, E or Y, or no amino acid,
$X_8$ is polar amino acid, such as E, K or T,
$X_9$ is polar amino acid, such as Y, D or N,
$X_{10}$ is aromatic amino acid, such as Y or H,
$X_{11}$ is small hydrophobic amino acid, such as V or A, and
$X_{12}$ is charged basic amino acid, such as K or R; and c) sequence $X_1X_2X_3X_4X_5X_6X_7X_8X_9X_{10}X_{11}X_{12}D\ Y$ (SEQ ID NO 3), wherein
$X_1$ is charged acidic amino acid, such as D or E,
$X_2$ is small or hydrophobic amino acid, such as A, G, K, P or Y,
$X_3$ is aromatic or small amino acid, such as W, F, G or N,
$X_4$ is aromatic or small amino acid, such as F or G , or no amino acid
$X_5$ is small amino acid, such as G or S, or no amino acid,
$X_6$ is small amino acid, such as G, or no amino acid,
$X_7$ is small polar amino acid, such as T, or no amino acid,
$X_8$ is polar aromatic amino acid, such as Y, or no amino acid,
$X_9$ is charged acidic or aromatic amino acid such as E or F, or no amino acid,
$X_{10}$ is aromatic or small amino acid, such as F, G, S, V or W,
$X_{11}$ is small or polar aromatic amino acid, such as Y or G, and
$X_{12}$ is aromatic or aliphatic hydrophobic amino acid, such as F or I.

More specifically, the present invention provides a fully human anti-VAP-1 antibody heavy chain comprising a first CDR amino acid sequence selected from the group consisting of SEQ ID NO:s 4 to 8 and their conservative sequence variants, and/or a second CDR amino acid sequence selected from the group consisting of SEQ ID NO:s 9 to 13 and their conservative sequence variants, and/or a third CDR amino acid sequence selected from the group consisting of SEQ ID NO:s 14 to 1 8 and their conservative sequence variants. Particular antibody heavy chains according to the present embodiments comprise a variable region selected from the group consisting of SEQ ID NO:s 19 to 23, and their conservative sequence variants.

The present invention further provides a fully human anti-VAP-1 antibody light chain comprising at least one CDR consensus sequence selected form the group consisting of:

a) sequence R A S Q $X_1X_2$S $X_3X_4X_5$L A (SEQ ID NO 24), wherein
$X_1$ is small amino acid, such as G or S,
$X_2$ is aliphatic amino acid, such as I or V,
$X_3$ is small polar or positively charged amino acid, such as S or R,
$X_4$ is small polar amino acid, such as S, or no amino acid, and
$X_5$ is small hydrophobic or aromatic hydrophobic amino acid, such as A, F, W or Y;

b) sequence $X_1$A S $X_2X_3X_4X_5$ (SEQ ID NO 25), wherein
$X_1$ is small acidic or small amino acid, such as D or G,
$X_2$ is small polar amino acid, such as S or N,
$X_3$ is aliphatic or positively charged amino acid, such as L or R,
$X_4$ is small or polar amino acid, such as A, E or Q, and
$X_5$ is polar or positively charged amino acid, such as S, T or R; and c) sequence Q Q $X_1X_2X_3X_4$P $X_5$T (SEQ ID NO 26), wherein
$X_1$ is aromatic or positively charged amino acid, such as F, Y or R,
$X_2$ is small amino acid, such as N, G or S,
$X_3$ is small polar amino acid, such as S or N,
$X_4$ is aromatic or small polar amino acid, such as Y, F, W or S, and
$X_5$ is aliphatic or positively charged amino acid, such as L or R.

More specifically, the present embodiments provide a fully human anti-VAP-1 antibody light chain comprising a first CDR amino acid sequence selected from the group consisting of SEQ ID NO:s 27 to 31 and their conservative sequence variants, and/or a second CDR amino acid sequence selected from the group consisting of SEQ ID NO:s 32 to 36 and their conservative sequence variants, and/or a third CDR amino acid sequence selected from the group consisting of SEQ ID NO:s 37 to 41 and their conservative sequence variants. Particular antibody heavy chains according to the present embodiments comprise a variable region selected from the group consisting of SEQ ID NO:s 42 to 46 and their conservative sequence variants.

A further aspect of the present invention is to provide a fully human anti-VAP-1 antibody comprising heavy and light chains according to the present embodiments. The antibody molecules and the chains of the present embodiments may comprise: a complete natural antibody molecule, having full length heavy and light chains; a fragment thereof, such as a Fab, Fab', F(ab')2 or Fv fragment; a light chain or heavy chain monomer or dimer; or a single chain antibody, e.g. a single chain Fv in which heavy and light chain variable regions are joined by a peptide linker; or any other recombinant, or CDR-grafted molecule. Similarly the heavy and light chain variable region may be combined with other antibody domains as appropriate.

It is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence.

Accordingly, the present disclosure provides monoclonal antibodies comprising one or more heavy and/or light chain CDR3 domains from an antibody derived from a human or non-human animal, wherein the monoclonal antibody is capable of specifically binding to VAP-1. Within certain aspects, the present disclosure provides monoclonal antibodies comprising one or more heavy and/or light chain CDR3 domains from a non-human antibody, such as a mouse or rat antibody, wherein the monoclonal antibody is capable of specifically binding to VAP-1. Within some embodiments, such inventive antibodies comprising one or more heavy and/or light chain CDR3 domain from a non-human antibody (a) are capable of competing for binding with; (b) retain the functional characteristics; (c) bind to the same epitope; and/or (d) have a similar binding affinity as the corresponding parental non-human antibody.

Within other aspects, the present disclosure provides monoclonal antibodies comprising one or more heavy and/or light chain CDR3 domain from a human antibody, such as, for example, a human antibody obtained from a non-human animal, wherein the human antibody is capable of specifically binding to VAP-1. Within other aspects, the present disclosure provides monoclonal antibodies comprising one or more heavy and/or light chain CDR3 domain from a first human antibody, such as, for example, a human antibody obtained from a non-human animal, wherein the first human antibody is capable of specifically binding to VAP-1 and wherein the CDR3 domain from the first human antibody replaces a CDR3 domain in a human antibody that is lacking binding specificity for VAP-1 to generate a second human antibody that is capable of specifically binding to VAP-1. Within some embodiments, such inventive antibodies comprising one or more heavy and/or light chain CDR3 domain from the first human antibody (a) are capable of competing for binding with; (b) retain the functional characteristics; (c) bind to the same epitope; and/or (d) have a similar binding affinity as the corresponding parental first human antibody.

The antibodies of the present disclosure may be further characterized by the various physical properties of the anti-VAP-1 antibodies.

Various assays may be used to detect and/or differentiate different classes of antibodies based on these physical properties.

In some embodiments, antibodies of the present disclosure may contain one or more glycosylation sites in either the light or heavy chain variable region. The presence of one or more glycosylation sites in the variable region may result in increased immunogenicity of the antibody or an alteration of the pharmacokinetics of the antibody due to altered antigen binding as well known in the art. Glycosylation has been known to occur at motifs containing an N-X-S/T sequence. Variable region glycosylation may be tested using a Glycoblot assay, which cleaves the antibody to produce a Fab, and then tests for glycosylation using an assay that measures periodate oxidation and Schiff base formation. Alternatively, variable region glycosylation may be tested using Dionex light chromatography (Dionex-LC), which cleaves saccharides from a Fab into monosaccharides and analyzes the individual saccharide content. In some instances, it is preferred to have an anti-VAP-1 antibody that does not contain variable region glycosylation. This can be achieved either by selecting antibodies that do not contain the glycosylation motif in the variable region or by mutating residues within the glycosylation motif using standard techniques well known in the art.

In an embodiment, the antibodies of the present disclosure do not contain asparagine isomerism sites. A deamidation or isoaspartic acid effect may occur on N-G or D-G sequences, respectively. The creation of isoaspartic acid can be measured using an iso-quant assay, which uses a reverse-phase HPLC to test for isoaspartic acid.

Each antibody will have a unique isoelectric point (pl), but generally antibodies will fall in the pH range of between 6 and 9.5. The pl for an IgG1 antibody typically falls within the pH range of 7-9.5 and the pl for an IgG4 antibody typically falls within the pH range of 6-8. Antibodies may have a pl that is outside this range. The isoelectric point may be tested using a capillary isoelectric focusing assay, which creates a pH gradient and may utilize laser focusing for increased accuracy as well known in the art. In some instances, it is preferred to have an anti-VAP-1 antibody that contains a pl value that falls in the normal range. This can be achieved either by selecting antibodies with a pl in the normal range, or by mutating charged surface residues using standard techniques well known in the art.

Each antibody will have a melting temperature that is indicative of thermal stability. A higher thermal stability indicates greater overall antibody stability in vivo. The melting point of an antibody may be measured using techniques such as differential scanning calorimetry. TM1 indicates the temperature of the initial unfolding of the antibody. TM2 indicates the temperature of complete unfolding of the antibody. Generally, it is preferred that the TM1 of an antibody of the present disclosure is greater than 60° C., preferably greater than 65° C., even more preferably greater than 70° C. Alternatively, the thermal stability of an antibody may be measured using circular dichroism as well known in the art.

In one embodiment, antibodies are selected that do not rapidly degrade. Fragmentation of an anti-VAP-1 antibody may be measured using capillary electrophoresis (CE) and Matrix Assisted Laser Desorption Ionisation Mass Spectrometry (MALDI-MS), as is well understood in the art.

In another embodiment, antibodies are selected that have minimal aggregation effects. Aggregation may lead to triggering of an unwanted immune response and/or altered or unfavorable pharmacokinetic properties. Generally, antibodies are acceptable with aggregation of 25% or less, preferably 20% or less, even more preferably 15% or less, even more preferably 10% or less and even more preferably 5% or less. Aggregation may be measured by several techniques well known in the art, including size-exclusion column (SEC) high performance liquid chromatography (HPLC), and light scattering to identify monomers, dimers, trimers or multimers.

The antibodies according to some embodiments of the present invention are preferably of IgG-type and more preferably of IgG4-type. However, other antibody isotypes, such as IgG1, IgG2, IgG3, IgM and IgE, are included.

In some embodiments, an antibody according to the present invention comprises heavy and light chain variable regions comprising amino acid sequences that are homologous to the amino acid sequences of the preferred antibodies described herein, and wherein the antibodies retain the desired functional properties of the anti-VAP-1 antibodies of embodiments of the invention.

For example, the invention provides an isolated monoclonal antibody, or antigen binding portion thereof, comprising a heavy chain variable region and a light chain variable region, wherein: (a) the heavy chain variable region comprises an amino acid sequence that is at least 80% homologous to an amino acid sequence selected from the group consisting of SEQ ID NO:s 19 to 23; (b) the light chain variable region comprises an amino acid sequence that is at least 80% homologous to an amino acid sequence selected from the group consisting of SEQ ID NO:s 42 to 46; (c) the antibody binds to human VAP-1 with a Kd of $1\times10^{-7}$ M or lower.

In other embodiments, the VH and/or VL amino acid sequences may be 85%, 90%, 95%, 96%, 97%, 98% or 99% homologous to the sequences set forth above. An antibody having VH and VL regions having high (i.e., 80% or greater) homology to the VH and VL regions of the sequences set forth above, can be obtained by mutagenesis (e.g., site-directed or PCR-mediated mutagenesis) of nucleic acid molecules encoding SEQ ID NO:s 19 to 23 and 42 to 46, followed by testing of the encoded altered antibody for retained function.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using standard methods known in the art.

In some embodiments, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the embodiments may be chemically modified (e.g., one or more chemical moieties can be attached to the antibody) or be modified to alter its glycosylation, again to alter one or more functional properties of the antibody.

For example, the Fc region may be altered by replacing at least one amino acid residue selected from amino acid residues 234, 235, 236, 237, 297, 318, 320 and 322 (the numbering of residues in the Fc region is that of the EU index of Kabat) can be replaced with a different amino acid residue such that the antibody has an altered affinity for an effector ligand but retains the antigen-binding ability of the parent antibody. The effector ligand to which affinity is altered can be, for example, an Fc receptor or the CI component of complement. This approach is described in further detail e.g. in U.S. Pat. Nos. 5,624,821 and 5,648,260.

Another modification of the antibodies herein that is contemplated by the embodiments is pegylation. An antibody can be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation may be carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (CI-CIO) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of embodiments of the invention.

In some embodiments, the present invention provides specific fully human anti-VAP-1 antibodies 8C10, 8A4, 3F10, 4B3 and 5F12. In other embodiments, the present invention provides recombinant fully human antiVAP-1 antibodies, such as recombinant 8C10, 8A4, 3F10, 4B3 and 5F12. In recombinant r8C10 (BTT-1023), the heavy chain consists of the amino acid sequence depicted in SEQ ID NO: 47 and the light chain consists of the amino acid sequence depicted in SEQ ID NO: 48.

TABLE 1

Fully human anti-VAP-1 amino acid sequences

| SEQ ID NO | Sequence description |
| --- | --- |
| 1 | Heavy chain CDR1 consensus |
| 2 | Heavy chain CDR2 consensus |
| 3 | Heavy chain CDR3 consensus |
| 4 | 8C10 heavy chain CDR1 |
| 5 | 8A4 heavy chain CDR1 |
| 6 | 3F10 heavy chain CDR1 |
| 7 | 5F12 heavy chain CDR1 |
| 8 | 4B3 heavy chain CDR1 |
| 9 | 8C10 heavy chain CDR2 |
| 10 | 8A4 heavy chain CDR2 |
| 11 | 3F10 heavy chain CDR2 |
| 12 | 5F12 heavy chain CDR2 |
| 13 | 4B3 heavy chain CDR2 |
| 14 | 8C10 heavy chain CDR3 |
| 15 | 8A4 heavy chain CDR3 |
| 16 | 3F10 heavy chain CDR3 |
| 17 | 5F12 heavy chain CDR3 |
| 18 | 4B3 heavy chain CDR3 |
| 19 | 8C10 heavy chain variable region |
| 20 | 8A4 heavy chain variable region |
| 21 | 3F10 heavy chain variable region |
| 22 | 5F12 heavy chain variable region |
| 23 | 4B3 heavy chain variable region |
| 24 | Light chain CDR1 consensus |
| 25 | Light chain CDR2 consensus |
| 26 | Light chain CDR3 consensus |
| 27 | 8C10 light chain CDR1 |
| 28 | 8A4 light chain CDR1 |
| 29 | 3F10 light chain CDR1 |
| 30 | 5F12 light chain CDR1 |
| 31 | 4B3 light chain CDR1 |
| 32 | 8C10 light chain CDR2 |
| 33 | 8A4 light chain CDR2 |
| 34 | 3F10 light chain CDR2 |
| 35 | 5F12 light chain CDR2 |
| 36 | 4B3 light chain CDR2 |
| 37 | 8C10 light chain CDR3 |
| 38 | 8A4 light chain CDR3 |
| 39 | 3F10 light chain CDR3 |
| 40 | 5F12 light chain CDR3 |
| 41 | 4B3 light chain CDR3 |
| 42 | 8C10 light chain variable region |
| 43 | 8A4 light chain variable region |
| 44 | 3F10 light chain variable region |
| 45 | 5F12 light chain variable region |
| 46 | 4B3 light chain variable region |
| 47 | Recombinant r8C10 heavy chain |
| 48 | Recombinant r8C10 light chain |

Fully human anti-VAP-1 antibodies may be prepared by immunizing mice in which the native mouse immunoglobulin genes have been inactivated and functionally replaced with all or part of the human immunoglobulin gene repertoire. Such mice are immunized with VAP-1 antigen and human antibody producing hybridomas are then generated from the mice using normal procedures. Cloned hybridoma cells which produce monoclonal antibodies that are reactive with VAP-1 antigen are then identified and expanded to produce purified fully human monoclonal antibodies.

Alternative ways to make a human antibody include transferring the specificity of an animal antibody to a human immunoglobulin. For example, mice are immunized with VAP-1 antigen and antibody producing hybridomas are then generated from the mice using normal procedures. Cloned hybridoma cells which produce monoclonal antibodies that are reactive with VAP-1 antigen are then identified and expanded to produce purified monoclonal antibodies. The cDNA sequences of the antibody heavy and light chain variable regions are determined and the complementarity determining regions (CDR) identified. The CDR amino acid sequences of the heavy and light chains are used to replace the matching CDR's of a human antibody, thus transferring the specificity of the rodent anti-VAP-1 antibody to a human antibody. The resulting anti-VAP-1 antibody is fully human in the sense that, although the original CDR amino acid sequences are derived from rodents, the same amino acid sequences are capable of being generated in a human derived antibody and cannot be accurately defined as being specific to rodents.

To generate hybridomas producing human monoclonal antibodies of some embodiments, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3X63-Ag8.653 nonsecreting mouse myeloma cells (ATCC, CRL 1580) with 50% PEG. Cells are plated at approximately $2 \times 10^5$ in flat bottom microtiter plate, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and IX HAT (Sigma; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be re-plated, screened again, and if still positive for human IgG, the monoclonal antibodies can be subcloned at least twice by limiting dilution. The stable subclones can then be cultured in vitro to generate small amounts of antibody in tissue culture medium for characterization. To purify human monoclonal antibodies, selected hybridomas can be grown in two-liter spinner-flasks for monoclonal antibody purification. Supernatants can be filtered and concentrated before affinity chromatography with protein A-SEPHAROSE™ (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

Fully human antibodies can also be produced from phage display libraries, which use genetically engineered phage to display and produce human antibody proteins on the surface of the recombinant phage. Single chain antibodies with high affinity and specificity to any given target are selected by screening and the antibody sequences can then be isolated from the phage to produce a recombinant fully human antibody. Such phage display methods for isolating human antibodies are established in the art.

Fully human monoclonal antibodies according to the present embodiments may also be prepared using SCID mice into which human immune cells have been reconstituted such that a human antibody response can be generated upon immunization. Such mice are described in, for example, U.S. Pat. Nos. 5,476,996 and 5,698,767.

When desired, DNA encoding the light and heavy chain variable regions of the antibody can be isolated and fused to the DNA encoding any desired human, or modified human, constant region in order to produce a DNA construct which can be inserted into an expression vector and transfected into a suitable expression host to produce a recombinant fully human antibody. Thus, antibodies according to the present embodiments may also be produced in a host cell transfectoma using, for example, a combination of recombinant DNA techniques and gene transfection methods as is well known in the art.

For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the VH segment is operatively linked to the heavy chain constant (CH) segment(s) within the vector and the VK segment is operatively linked to the light chain constant (CL) segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of some embodiments of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes, as well known in the art. It will be appreciated by those skilled in the art that the design of the expression vector, including the selection of regulatory sequences, may depend on such factors as the choice of the host cell to be transformed, the level of expression of protein desired, etc. Regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or β-globin promoter. Still further, regulatory elements composed of sequences from different sources, such as the SRalpha promoter system, which contains sequences from the SV40 early promoter and the long terminal repeat of human T cell leukemia virus type 1.

In addition to the antibody chain genes and regulatory sequences, the recombinant expression vectors of some embodiments may carry additional sequences, such as sequences that regulate replication of the vector in host cells (e.g., origins of replication) and selectable marker genes. As well known in the art, the selectable marker gene facilitates selection of host cells into which the vector has been introduced. For example, typically the selectable marker gene confers resistance to drugs, such as G418, hygromycin or methotrexate, on a host cell into which the vector has been introduced. Suitable selectable marker genes include the dihydrofolate reductase (DHFR) gene (for use in dhfr– host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the embodiments in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody.

Suitable mammalian host cells for expressing the recombinant antibodies of the invention include Chinese Hamster Ovary (CHO cells) (including dhfr– CHO cells know in the art), NS0 myeloma cells, COS cells and SP2 cells. When recombinant expression vectors encoding antibody genes are introduced into mammalian host cells, the antibodies may be produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

A further aspect of the present invention is to provide a DNA molecule encoding a fully human anti-VAP-1 antibody heavy chain variable region, comprising a first DNA sequence selected from the group consisting of SEQ ID NO:s 49 to 53, and their conservative sequence variants, and/or a second DNA sequence selected from the group consisting of SEQ ID NO:s 54 to 58, and their conservative sequence variants, and/or a third DNA sequence selected from the group consisting of SEQ ID NO:s 59 to 63, and their conservative sequence variants, said DNA sequences encoding CDR regions 1 to 3, respectively. According to a particular aspect, the present invention provides a DNA molecule encoding a heavy chain variable region and comprising a DNA sequence selected from the group consisting of SEQ ID NO:s 64 to 68 and their conservative sequence variants.

Still further aspect of the present invention is to provide a DNA molecule encoding a fully human anti-VAP-1 antibody light chain variable region, comprising a first DNA sequence selected from the group consisting of SEQ ID NO:s 69 to 73, and their conservative sequence variants, and/or a second DNA sequence selected from the group consisting of SEQ ID NO:s 74 to 78, and their conservative sequence variants, and/or a third DNA sequence selected from the group consisting of SEQ ID NO:s 79 to 83, and their conservative sequence variants, said DNA sequences encoding CDR regions 1 to 3, respectively. According to a particular aspect, the present invention provides a DNA molecule encoding a heavy chain variable region and comprising a DNA sequence selected from the group consisting of SEQ ID NO:s 84 to 88, and their conservative sequence variants.

In one embodiment, the present invention provides DNA molecules encoding recombinant fully human anti-VAP-1 antibodies, such as recombinant 8C10, 8A4, 3F10, 4B3 and 5F12. In recombinant r8C10 (BTT-1023), the heavy chain is encoded by DNA comprising the polynucleotide sequence depicted in SEQ ID NO: 89 and the light chain is encoded by DNA comprising the polynucleotide sequence depicted in SEQ ID NO: 90.

TABLE 2

Fully human anti-VAP-1 nucleotide sequences

| SEQ ID NO | Sequence description |
| --- | --- |
| 49 | 8C10 heavy chain CDR1 |
| 50 | 8A4 heavy chain CDR1 |
| 51 | 3F10 heavy chain CDR1 |
| 52 | 5F12 heavy chain CDR1 |
| 53 | 4B3 heavy chain CDR1 |
| 54 | 8C10 heavy chain CDR2 |
| 55 | 8A4 heavy chain CDR2 |
| 56 | 3F10 heavy chain CDR2 |
| 57 | 5F12 heavy chain CDR2 |
| 58 | 4B3 heavy chain CDR2 |
| 59 | 8C10 heavy chain CDR3 |
| 60 | 8A4 heavy chain CDR3 |
| 61 | 3F10 heavy chain CDR3 |
| 62 | 5F12 heavy chain CDR3 |
| 63 | 4B3 heavy chain CDR3 |
| 64 | 8C10 heavy chain variable region |
| 65 | 8A4 heavy chain variable region |
| 66 | 3F10 heavy chain variable region |
| 67 | 5F12 heavy chain variable region |
| 68 | 4B3 heavy chain variable region |
| 69 | 8C10 light chain CDR1 |
| 70 | 8A4 light chain CDR1 |
| 71 | 3F10 light chain CDR1 |
| 72 | 5F12 light chain CDR1 |
| 73 | 4B3 light chain CDR1 |
| 74 | 8C10 light chain CDR2 |
| 75 | 8A4 light chain CDR2 |
| 76 | 3F10 light chain CDR2 |
| 77 | 5F12 light chain CDR2 |
| 78 | 4B3 light chain CDR2 |
| 79 | 8C10 light chain CDR3 |
| 80 | 8A4 light chain CDR3 |
| 81 | 3F10 light chain CDR3 |
| 82 | 5F12 light chain CDR3 |
| 83 | 4B3 light chain CDR3 |
| 84 | 8C10 light chain variable region |
| 85 | 8A4 light chain variable region |
| 86 | 3F10 light chain variable region |
| 87 | 5F12 light chain variable region |
| 88 | 4B3 light chain variable region |
| 89 | Recombinant r8C10 heavy chain |
| 90 | Recombinant r8C10 light chain |

The present embodiments further provide expression vectors comprising nucleotide sequences described above. Suitable expression vectors include vectors containing elements important for the expression and secretion of proteins in mammalian host cells. The vector may comprise DNA encoding human heavy chain constant regions, or light chain constant regions, or both. The same vector may be used for the expression of both heavy and light chains or, alternatively, different vectors containing either heavy or light chain constant regions may be used.

In one embodiment according to the present invention, the expression vector comprises the heavy chain constant region of human IgG4, modified to reduce FcγRI-binding and antibody dependent cell mediated cytotoxicity (ADCC) by substituting amino acid leucine 235 for alanine, as described in U.S. Pat. No. 5,624,821. The numbering of residues in the Fc region is that of the EU index of Kabat.

The present embodiments still further provide host cells transfected with expression vectors according to the present embodiments. Any suitable host cell/vector system may be used for expression of the DNA sequences coding for the fully human antibody heavy and light chains. Bacterial e.g. *Escherichia coli*, and other microbial systems may be used, in particular for expression of antibody fragments such as Fab and F(ab')2 fragments, and especially Fv fragments and single chain antibody fragments e.g. single chain Fv's. Eukaryotic e.g. plant, yeast or mammalian host cell expression systems or transgenic plants and animals may be used for production of larger antibody products, including complete antibody molecules, and/or if glycosylated products are required. Suitable mammalian host cells include CHO (Chinese hamster ovary) cells and myeloma or hybridoma cell lines as set forth above. Preferred host cells are CHO cells.

A further aspect of the present invention is to provide a method for producing recombinant fully human anti-VAP-1 antibodies by a process which comprises transfecting a host cell with an expression vector comprising DNA sequences coding for the fully human antibody heavy and light chains according to the present embodiments under the control of suitable promotors and secretion signals, and propagating said host cell under such conditions that each chain is expressed, and isolating said expressed and assembled fully human anti-VAP-1 antibody or biologically active derivatives thereof from the culture. General methods by which the vectors may be constructed, transfection methods and culture methods are well known in the art.

The present invention further provides a pharmaceutical composition comprising a pharmaceutically acceptable carrier or diluent and, as active ingredient, a fully human anti-VAP-1 antibody according to the present embodiments. The composition of the present embodiments contain fully human anti-VAP-1 antibodies according to the present embodiments in amounts sufficient to antagonize (fully or partially) the patient's native VAP-1 binding to the biological ligands of VAP-1 in patients in need of such antagonizing, and specifically to VAP-1 ligands presented on leukocytes.

Amounts and regimens for the administration of fully human anti-VAP-1 antibodies according to the present embodiments may be determined readily by those with ordinary skill in the clinical art of treating inflammation-related disorders. Generally, the dosage of the fully human anti-VAP-1 antibody treatment will vary depending on considerations such as: age, gender and general health of the patient to be treated; kind of concurrent treatment, if any; frequency of treatment and nature of the effect desired; extent of tissue damage; duration of the symptoms; and other variables to be adjusted by the individual physician. A desired dose can be administered in one or more applications to obtain the desired results. Pharmaceutical compositions according to the present embodiments may be provided in unit dosage forms.

The pharmaceutical compositions according to the present embodiments may be administered in any appropriate pharmacological carrier for administration. They can be administered in any form that effects prophylactic, palliative, preventive or curing conditions of VAP-mediated medical conditions in human or animal patients.

Pharmaceutical compositions of the fully human anti-VAP-1 antibodies according to the present embodiments for parenteral and topical administration include sterile aqueous or non-aqueous solvents, suspensions and emulsions. Examples of non-aqueous solvents are propylene glycol, polyethylene glycol, vegetable oil, fish oil, and injectable organic esters. Aqueous carriers include water, water-alcohol solutions, including saline and buffered medial parenteral vehicles including sodium chloride solution, Ringer's dextrose solution, dextrose plus sodium chloride solution, Ringer's solution containing lactose, or fixed oils. Intravenous vehicles include fluid and nutrient replenishers, electrolyte replenishers, such as those based on Ringer's dextrose and the like. Aqueous compositions according to the embodiments may comprise suitable buffer agents, such as sodium and potassium phosphates, citrate, acetate, carbonate or glycine buffers depending on the targeted pH-range. The use of sodium chloride as a tonicity adjuster is also useful. Compositions may include other excipients, such as stabilizing agents or preservatives. Useful stabilizing excipients include surfactants (polysorbate 20 & 80, poloxamer 407), polymers (polyethylene glycols, povidones), carbohydrates (sucrose, mannitol, glucose, lactose), alcohols (sorbitol, glycerol propylene glycol, ethanolamine), antioxidants (ascorbic acid, cysteine etc.), chelating agents (EDTA salts, histidine, aspartic acid) or metal ions (Ca, Ni, Mg, Mn). Among useful preservative agents are benzyl alcohol, chlorbutanol, benzalkonium chloride and possibly parabens.

The pharmaceutical composition according to the present embodiments may be provided in concentrated form or in form of a powder to be reconstituted on demand. In such cases formulations of powder for solution for injection/infusion excipients mentioned above may be used. In case of lyophilizing, certain cryoprotectants are preferred, including polymers (povidones, polyethylene glycol, dextran), sugars (sucrose, glucose, lactose), amino acids (glycine, arginine, glutamic acid) and albumin. If solution for reconstitution is added to the packaging, it may consist e.g., of pure water for injection or sodium chloride solution or dextrose or glucose solutions.

The composition of the embodiments of the invention are suitable for diagnosing or treating any condition involving an inflammatory reaction in which VAP-1 adhesion plays a role in mediating the transmigration and infiltration of leukocytes from the blood into a site of inflammation. Thus, the composition is useful for diagnosing or treating inflammatory arthritides and connective tissue diseases such as reactive arthropathies, postinfective arthropathies, inflammatory polyarthropathies, systemic connective tissue disorders, inflammatory spondylopathies, myositis, synovitis, Reiter's disease, seropositive rheumatoid arthritis, other rheumatoid arthritis, extraarticular rheumatoid disease, psoriatic and enteropathic arthropathies, juvenile arthritis, unspecified arthritis, polyarteritis nodosa and related conditions, other necrotizing vasculopathies, dermatopolymyositis, systemic sclerosis, other diseases with systemic involvement of connective tissue, ankylosing spondylitis and other inflammatory spondylopathies. In addition, inflammatory bowel diseases such as Crohn's disease and ulcerative colitis, dermatoses such as bullous disorders, dermatitis, papulosquamous disorders, erythema, lichen scterosus et atrophicus, craurosis vulvae, discoid lupus erythematosus, morphea, Pemphigus, pemphigoid, dermatitis herpetiformis, atopic dermatitis, allergic contact dermatitis, irritant contact dermatitis, unspecified contact dermatitis, psoriasis, erythema multiforme, other inflammatory diseases such as multiple sclerosis, inflammatory neuropathy, inflammatory myopathy, acute disseminated encephalomyelitis, vasculitis of the central nervous system, Sjogrens syndrome, diabetes, systemic lupus erythematosus, asthma and inflammatory liver disease, Graves disease and thyroiditis, atherosclerosis, inflammation of the eye including uveitis, iritis, iridocyclitis, alcoholic hepatitis, allograft transplantation, xenograft transplantation, glomerulonephritis, reperfusion injury and acute inflammatory conditions following myocardial infarction and stroke may be suitable for diagnosing or treating by the composition of the present embodiments.

The therapeutically useful fully human anti-VAP-1 antibodies according to the present embodiments may be conjugated, either chemically or by genetic engineering, to other agents, which provide targeting of the antibodies to a desired site of action. Alternatively, other compounds may be conjugated, either chemically or by genetic engineering, to the antibodies according to the present embodiments, so as to enhance or provide additional properties to the antibodies, especially properties, which enhance the antibodies' ability to promote alleviation of harmful effects mediated by VAP-1 binding.

The fully human anti-VAP-1 antibodies according to the present embodiments may by labeled, either chemically or by genetic engineering, to provide detectable antibodies. Such labeled antibodies will be useful tools for imaging inflammatory sites in humans, especially for in vivo immunoscintigraphic imaging of inflammation sites. This type of imaging may replace the more cumbersome and expensive leukocyte imaging-method currently used. For imaging purposes, the use of antibody fragments may be preferable to the whole antibody approach to anti-inflammatory therapy and fragments derived from fully human antibodies should still be safer than their chimeric or mouse equivalents.

In another aspect, the present invention is directed to a method of lessening or treating inflammation, in vivo, in the human body, by administering, to a human patient in need of such treatment, efficacious levels of the fully human anti-VAP-1 antibody according to the present embodiments. The term "treatment" or "treating" is intended to include the administration of fully human anti-VAP-1 antibodies to a subject for purposes which may include prophylaxis, amelioration, prevention or cure of disorders mediated by VAP-1 adhesion events. The particular anti-VAP-1 antibodies that are the subject of the methods of some embodiments of the invention are purified recombinant fully human anti-VAP-1 antibodies of the present embodiments.

By an "efficacious level" of a fully human anti-VAP-1 antibody is meant a level in which the harmful effects of VAP-1 mediated events are, at a minimum, ameliorated. An efficient amount of the antibody of the present embodiments is one that is sufficient to block, or partially block, the endothelial binding of leukocytes in order to inhibit leukocytic infiltration to inflammatory sites, where such infiltration is harmful or undesired. Amounts and regimens for the administration of fully human anti-VAP-I antibodies can be determined readily by those with ordinary skill in the clinical art of treating inflammation-related disorders. Preferably, the fully human anti-VAP-1 antibodies according to the present embodiments are provided intravascularly at intervals ranging between once weekly to once every three months at doses in the range of 0.01 to 20 mg/kg, more preferably in the range of 0.1 to 10 mg/kg, most preferably 0.5 to 5 mg/kg. Alternatively, the fully human anti-VAP-1 antibodies according to the present embodiments are provided subcutaneously at intervals ranging between once weekly to once every three months at doses in the range of 0.1 to 20 mg/kg, more preferably in the range of 0.2 to 10 mg/kg, most preferably 0.5 to 5 mg/kg.

The following examples are given to further clarify the embodiments of the invention in more detail but are not intended to restrict the scope of the present invention. Further applications and uses are readily apprehended by a person skilled in the art, i.e., clinicians familiar with inflammatory disorders and treatment thereof.

EXAMPLES

Example 1

Isolation of Human Anti-VAP-1 Monoclonal Antibody Expressing Hybridomas

A human immunoglobulin transgenic mouse strain (HUMAB MOUSE®; Medarex Inc.) was used to develop human anti-VAP-1 monoclonal antibody expressing hybridoma cells. The HUMAB MOUSE® contains human immunoglobulin gene miniloci that encode unrearranged human heavy (μ and γ) and κ light chain immunoglobulin sequences, together with targeted mutations that inactivate the endogenous μ and κ chain loci (see e.g., Lonberg, et al. (1994) Nature 368(6474): 856-859). Accordingly, the mice exhibit reduced expression of mouse IgM or K, and in response to immunization, the introduced human heavy and light chain transgenes undergo class switching and somatic mutation to generate high affinity human IgG κ monoclonal antibody. The preparation and use of HuMab mice, and the genomic modifications carried by such mice, is described e.g. in U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al; PCT Publications WO 92/03918, WO 93/12227, WO 94/25585, WO 97/13852, WO 98/24884 and WO 99/45962, all to Lonberg and Kay; and PCT Publication WO 01/14424 to Korman et al.

When immunized with recombinant human VAP-1 (rhVAP-1), this transgenic mouse produces human IgG antibodies specific to human VAP-1.

The immunization scheme was as follows: mice were immunized by multiple intraperitoneal and subcutaneous injections of rhVAP-1 purified from CHO cells stably transfected with an expression plasmid containing a human VAP-1 cDNA and expressing human VAP-1 (Smith et al., J. Exp. Med. (1998) 188:17-27) mixed with complete Freunds adjuvant followed by rhVAP-1 mixed with incomplete Freunds adjuvant or rhVAP-1 mixed with Ribi adjuvant. Serum samples from immunized mice were analyzed for immune status monitoring by antibody capture ELISA using immobilized rhVAP-1 and Fluorometric Microvolume Assay Technology (FMAT) using CHO cells stably transfected with an expression plasmid containing a human VAP-1 cDNA and expressing human VAP-1. Final boost injections of rhVAP-1 were administered intravenously and intraperitoneally prior to splenectomy.

Human anti-VAP-1 monoclonal antibody expressing hybridomas were derived by fusing P3x63Ag8.653 myeloma cells (ATCC CRL 1580) with splenocytes from mice immunized as above using polyethyleneglycol (PEG) as fusionogen. Hybridoma supernatants were initially screened by ELISA for presence of human IgG antibodies with a kappa light chain. Human IgG positive cells were then screened by ELISA on rhVAP-1 and by FMAT for binding to VAP-1 expressed on the surface of CHO cells stably transfected with an expression plasmid containing a human VAP-1 cDNA. Five human anti-VAP-1 IgG$_1$ hybridoma clones, namely 5F12, 4B3, 3F10, 8A4 and 8C10 were selected.

Example 2

VAP-1 Binding Properties of the Fully Human Antibodies 5F12, 4B3, 3F10, 8A4 and 8C10

A time-resolved immunofluorometric assay was used quantitatively to examine the binding of 5F12, 4B3, 3F10, 8A4 and 8C10 to rhVAP-1. A microtiter plate was coated with rhVAP-1 and then blocked with bovine serum albumin solution. An amount of antibody between 2 and 4320 ng/ml was subsequently added to bind to rhVAP-1 and the bound antibody detected by a europium-conjugated mouse anti-human antibody (Perkin Elmer Inc.). The label was detected by measuring the time-resolved fluorescence (VICTOR$^3$™ multilabel counter, PerkinElmer Inc.) at 615 nm. The fluorescence counts directly correlate with how much antibody was bound to its target. The sample data were then analyzed in comparison to the standard curve of a reference. The data show that 5F12, 4B3, 3F10, 8A4 and 8C10 bind to rhVAP-1 and the affinities (Kd) are shown in Table 3.

TABLE 3

| Binding of 5F12,4B3, 3F10, 8A4 and 8C10 mAbs to rhVAP-1 | |
|---|---|
| mAb | Kd (nM) |
| 8C10 | 0.21 |
| 3F 10 | 0.25 |
| 4B3 | 0.31 |
| 8A4 | 0.28 |
| 5F12 | 0.65 |

Example 3 cDNA Preparation, Cloning and Sequencing of the Variable Regions of the Fully Human Antibodies 5F12, 4B3, 3F10, 8A4 and 8C10

In order to construct recombinant antibodies, the cDNAs encoding the human heavy and light chains variable regions from the antibodies obtained in Example 1 were isolated and cloned into plasmid vectors for sequence analysis.

cDNA clones of human immunoglobulin (Ig) heavy chain variable ($V_H$) and light chain variable ($V_L$) regions were derived from the anti-VAP-1 expressing hybridoma cells 5F12, 4B3, 3F10, 8A4 and 8C10 in the following way. Total RNA was prepared from 5×10$^6$ hybridoma cells using the RNEASY® kit from Qiagen. $V_L$ and $V_H$ cDNAs were prepared by reverse transcription of RNA followed by "rapid amplification of cDNA ends (RACE)" procedure using "SMART™ RACE cDNA amplification kit" and high fidelity "ADVANTAGE®-HF 2 PCR kit" from BD Biosciences Clontech. The PCR amplified products were then purified, cloned into vector pCR4-TOPO® TA (Invitrogen) and transformed into *E. coli* strain, TOP10 (Invitrogen). Miniprep DNA's for plasmid clones of $V_L$ and $V_H$ for each of 5F12, 4B3, 3F10, 8A4 and 8C10 were sequenced and the nucleotide and deduced corresponding protein sequences are shown in FIGS. 1 to 6.

Example 4

Construction of a Mammalian Expression Vector to Express Recombinant r8C10 mAb

The 8C10 variable regions were inserted into an appropriate mammalian expression vector containing appropriate heavy and light chain constant regions, as described below, in order to produce a functional recombinant r8C10 antibody (named BTT-1023) in CHO cells.

The Fc region of an antibody is known to determine the ability of antibody/antigen complexes to direct immune responses. The aim was to produce therapeutic antibodies which would block the binding of leukocytes to vascular endothelium and not recruit any effector functions. Therefore the heavy chain constant region of human IgG4, modified to reduce FcγRI-binding and antibody dependent cell mediated cytotoxicity (ADCC) by substituting amino acid leucine 235 for alanine, as described in U.S. Pat. No. 5,624,821, was used in the expression vector. The 8C10 $V_L$ and $V_H$ cDNA's were amplified to contain appropriate cloning sites and an optimal Kozak consensus sequence at the 5' end using PCR Supermix (Invitrogen). Forward and reverse PCR primers were designed to have appropriate restriction sites for cloning. The PCR products, which include the native $V_L$ and $V_H$ signal sequences respectively, were purified and cloned into a plasmid vector carrying a human kappa light chain constant region and a human gamma 4 heavy chain containing the mutations serine 228 to proline and leucine 235 to alanine and called pICO-g4PA(VAP1.8C10), generating plasmids which were then transformed into E. coli TOP10 cells. The $V_L$ and $V_H$ regions of the plasmid were sequenced to confirm the integrity of the cloned PCR products.

The 8C10 light chain was amplified by PCR to contain a HindIII cloning site and an optimal Kozak consensus sequence at the 5' end, and an EcoRI cloning site at the 3' end, utilizing the pICO-g4PA(VAP1.8C10) plasmid as the template and PCR Supermix. The PCR product, which includes the native 8C10 light chain signal sequence, was digested with HindIII and EcoRI, purified and cloned into the expression vector pEE12.4, which was obtained from Lonza Biologics, at HindIII and EcoR I sites, generating plasmid 2116. The 2116 plasmid was transformed into DH5α™ Max Efficiency (Invitrogen Inc.) competent E. coli cells.

The 8C10 heavy chain was amplified by PCR to contain a HindIII cloning site and an optimal Kozak consensus sequence at the 5' end, and an EcoRI cloning site at the 3' end, utilizing pICO-g4PA(VAP1.8C10) plasmid as the template and PCR Supermix. The PCR product, which includes the native 8C10 heavy chain signal sequence, was digested with HindIII and EcoRI. The 8C10 heavy chain containing fragment was purified and cloned into Lonza vector pEE6.4, which was obtained from Lonza Biologics, at HindIII and EcoRI sites, generating plasmid 2117. The 2117 plasmid was transformed into DH5a Max efficiency competent cells. Plasmids 2116 and 2117 were digested with SalI and NotI, and the largest fragment from each digest was ligated using T4 DNA ligase resulting in plasmid 2118 [2118-pEE12.4-VAP1 (8C10)]. Plasmid 2118 was transformed into DH5α Max efficiency competent cells. The entire heavy and light chain encoding DNA was sequenced to confirm the sequence accuracy and integrity.

Example 5

Expression of the Recombinant Fully Human Antibody BTT-1023 in CHO Cells

The fully human antibody BTT-1023 was produced from CHO cells as follows. 2118-pEE12.4-VAP1(8C10) plasmid DNA was linearized with PvuI. The DNA was transfected by electroporation into CHOKISV cells obtained from Lonza Biologics. The cells were then plated at 50 μL/well in 96-well plates ($2.5 \times 10^3$ cells/well) in chemically defined (CD) CHO (Catalog number #040119, Gibco Invitrogen Inc.) post-transfection medium (L-glutamine free CD CHO+1×GS (glutamine synthetase) supplement+2.16 mg/L thymidine). Plates were then fed 24 hours later with 150 μL/well of CD CHO selection medium (L-glutamine free CD CHO+1×GS supplement+2.16 mg/L thymidine+66.6 μM MSX (methionine sulfoximine) or 133.3 μM MSX) resulting in a final 50 μM or 100 μM overall MSX concentration. The levels of antibody production by MSX resistant colonies were measured by a human IgG sandwich ELISA. Colonies producing high levels of antibody were selected for expansion in CD CHO expansion media (L-glutamine free CD CHO+1×GS supplement+2.16 mg/L thymidine+50 μM MSX or 100 μM MSX), first to 24-well plates, then to T-flasks. The cells were expanded in shake flasks prior to preparation of a 5-vial transfectoma cell bank (TCB). Cell line 15B7 was selected from the 50 μM MSX plates and was maintained in CD CHO expansion media containing 50 μM MSX. Antibody was produced by culturing the transfected CHO cells as above to generate conditioned medium from which BTT-1023 could be purified using standard techniques for purifying monoclonal antibodies from culture supernatant.

Example 6

Binding Properties of the Recombinant Fully Human Antibody BTT-1023

A time-resolved immunofluorometric assay was used to quantitatively examine the binding of BTT-1023 to rhVAP-1. A microtiter plate was coated with rhVAP-1 and then blocked with bovine serum albumin solution. An amount of BTT-1023 between 2 and 4320 ng/ml was subsequently added to bind to VAP-1 and the bound BTT-1023 detected by a europium-conjugated mouse anti-human antibody (PerkinElmer Inc.). The label was detected by measuring the time-resolved fluorescence (VICTOR³™ multilabel counter, PerkinElmer Inc.) at 615 nm. The fluorescence counts directly correlate with how much BTT-1023 was bound to its target. The sample data were then analyzed in comparison to the standard curve of a reference. The data show that BTT-1023 binds to recombinant human VAP-1 with an affinity (Kd) of 0.38 nM.

A real time direct binding assay using a BIACORE® surface plasmon resonance assay was used to analyse the binding kinetics of rhVAP-1 to BTT-1023. Biotinylated protein G' (Sigma) immobilized on a streptavidin coated chip (BIACORE® AB) was used to capture BTT-1023 from the mobile phase. Each run consisted of two sequential phases: an injection of BTT-1023 mAb and an injection of ligand binding analyte (rhVAP-1). Constant amounts of rhVAP-1 were used as an analyte for saturating concentration of mAbs (ligands). Experiments were performed using BIALITE® equipment (BIACORE® AB) and the data analyzed using Biacore software. The data show that recombinant human VAP-1 binds to BTT-1023 with an affinity (Kd) of 0.13 nM.

The binding of the fully human BTT-1023 to human VAP-1 was analyzed by immunofluorescence staining and flow cytometry. For flow cytometry, transfected cells from a rat endothelial cell line (Ax cells) expressing human VAP-1 cDNA (Smith et al., J. Ex. Med. (1998) 188:17-27) were used. These were grown in 175 cm³ flasks in RPMI 1640 medium (Sigma) supplemented with 20% FCS (fetal calf serum), 2 mM L-glutamine, 1 mM Na-pyruvate, 10 µM β-ME (beta-mercaptoethanol), 1% non-essential amino acids, 100 U/ml penicillin, 100 µg/ml streptomycin and 0.75 mg/ml GENETICIN™. In order to release the cells, they were washed twice with PBS (phosphate buffered saline) and incubated in 10 ml Cell Dissociation Buffer (GibcoBRL) for 3 min at 37° C. After addition of 10 ml of medium, the cells were pelleted (5 min, 1000 g, at room temperature), resuspended in Wash buffer [PBS, 0.1% (w/v) BSA (bovine serum albumin), 0.1% (v/v) NaN$_3$] at $10^6$ cells/ml and kept on ice.

Cell suspension (100 µl/well) was transferred into 96-well plates, the cells pelleted (4 min, 1000 g, 10° C.) and 100 µl aliquots of antibody solution added into the wells. After a 30-min incubation on ice, the cells were washed trice with 150 µl wash buffer/well and then incubated with 100 µl of 39 µg/ml FITC-conjugated (fluorescein isothiocyanate) anti-human IgG (Fc-specific, Sigma) for 30 min on ice. Finally, the cells were washed as earlier and fixed by adding 100 µl of Wash Buffer with 1% (v/v) formaldehyde and kept at 4° C. until analysis in a flow cytometer. Control samples were stained with FITC-conjugated anti-human IgG secondary antibody alone.

All flow cytometry samples were analyzed on a FACS-CAN™ (Becton Dickinson). For each sample, data for a minimum of 10 000 gated events were collected and the geometric mean channel of fluorescence calculated using Lysys II software.

BTT-1023 bound specifically to human VAP-1 as shown by staining 10 of transfected Ax cells which express VAP-1 on their surface. (FIG. 7).

Example 7

Functional Characteristics of BTT-1023

An in vitro transmigration assay was used to test the functional capacity of BTT-1023 to inhibit leukocyte transmigration through an endothelial monolayer. A monolayer of Ax rat endothelial cells, transfected so as to express recombinant human VAP-1 on their surface, was grown in the upper chamber of a TRANSWELL® apparatus (Becton Dickinson). Freshly isolated human peripheral blood mononuclear cells were placed in the top chambers and allowed to migrate towards the monocyte chemoattractant peptide fMLP (N-formyl-methionyl-leucyl-phenylalanine, 100 nM) in the bottom chambers for 2 h. The monolayers were treated with either BTT-1023 or with BTT-1008, a non-binding negative control antibody with a human constant region (Kirton et al., Eur. J. Immunol. (2005) 35:3119-30) or with BTT-1002, a positive control chimeric anti-VAP-1 mAb known to block VAP-1 mediated adhesion and transmigration. Cells migrated through the monolayer were collected from the bottom chamber and counted microscopically. BTT-1023 significantly reduced the migration of cells through the endothelial cell monolayer at 10 ng ml$^{-1}$, and blocked migration at 1 µg/ml$^{-1}$. Negative control antibody BTT-1008 had no effect at 0.1 µg/ml$^{-1}$ whereas positive control BTT-1002 also blocked transmigration completely at 1 µg/ml$^{-1}$ as seen in FIG. 8.

Example 8

Improved Pharmacokinetic Properties of the Recombinant Fully Human Antibody BTT-1023 Compared to the Chimeric Antibody BTT-1002

Two female marmosets (non human primates) were administered 25 mg/kg BTT-1023 each, by bolus intravenous injection. Blood samples for analysis of BTT-1023 concentration were collected 10 minutes, 1, 3, 6, 24, 48, 72 and 144 hours after dosing.

A time-resolved immunofluorometric assay for quantification of analyte (either BTT-1002 or BTT-1023) concentration in marmoset serum utilizes a biotin-conjugated analyte-specific rabbit polyclonal antibody as a capturer on a streptavidin coated microtiter plate. Such polyclonal antibodies were made by repeated immunisation of rabbits with either BTT-1002 or BTT-1023, collection of serum and affinity purification of the resulting anti-BTT-1002 or anti-BTT-1023 polyclonal antibodies. Detection of bound analyte was done using a europium-conjugated secondary antibody. The label was detected by measuring the time-resolved fluorescence (VICTOR$^3$™ multilabel counter, PerkinElmer Inc.) at 615 nm. The fluorescence counts directly correlate with how much analyte was present in the sample. The sample data were then analyzed in comparison to the standard curve of a reference.

Pharmacokinetic parameters were determined using non-compartmental analysis. When compared to data derived from a similar study performed with BTT-1002, in which 40 mg/kg was administered intravenously to each of two female marmosets, the fully human VAP-1 antibody shows improved pharmacokinetic properties with an improved serum concentration over time (AUC) profile and an extended elimination half-life (Table 4).

TABLE 4

Pharmacokinetic properties of BTT-1023 compared to BTT-1002

| Dose (mg/kg) | AUC $_{(0-last)}$ (ug*h/mL) | AUC $_{(0-\infty)}$ (ug*h/m L) | t $_{1/2}$(h) | V$_d$ (ml/kg) |
|---|---|---|---|---|
| 25 of BTT-1023 | 33200 | 55100 | 120 | 71 |
| 25 of BTT-1023 | 20600 | 23900 | 53 | 69 |
| 40 of BTT-1002 | 19100* | 19100* | 25* | 75* |

*mean of n = 2

Example 9

Pharmaceutical Compositions of the Fully Human Antibodies

Examples of a pharmaceutical composition comprising a fully human anti-VAP-1 antibody according to the present embodiments, suitable for parenteral administration, given as a solution for injection or for infusion or as a concentrate for such a solution.

| Percentual amount of ingredient to 1 ml | |
|---|---|
| anti-VAP-1 antibody | 0.1-10% |
| Sodium chloride or potassium chloride | 0.5-1.5% |
| Disodium hydrogen phosphate dihydrate | 0.1-2% |
| Sodium or potassium dihydrogen phosphate | 0.1-2% |
| Sucrose | 0.5-10% |
| Polysorbate 20 or 80 | 0.01-1% |
| Water for injection | to 1 ml |
| anti-VAP-1 antibody | 0.1-10% |
| Sodium chloride | 0.5-1.5% |
| EDTA/DTPA | 0.01-1.5% |
| Mannitol | 0.1-5% |
| Polysorbate 20 or 80 | 0.01-1% |
| Sodium citrate as dihydrate | 0.5-5% |
| Water for injection | to 1 ml |

Example 10

Efficacy of Fully Human Antibodies in in vivo Models of Inflammation

Efficacy of Fully Human VAP-1 Antibody Treatment in Collagen-induced Arthritis in the Rhesus Monkey The effect of the fully human antibodies is assessed in the model of collagen-induced arthritis (CIA) in the rhesus monkey aiming at gathering data on the usefulness of BTT-1023 antibody in arthritic indications.

Adult rhesus monkeys, negative in terms of MHC A26, which have a CIA incidence of 99%, immunized with bovine type II collagen, are selected to the study. Ten animals are divided into two groups of five animals. Arthritis is induced by injecting 3-5 mg of bovine collagen in Freund's complete adjuvant in 10 spots in the animal's back. Using this approach arthritis is clinically evident at 3-5 weeks after immunization and lasts normally 7-9 weeks.

The intravenous treatment of four weeks with the fully human antibodies at doses between 1 and 50 mg/kg twice weekly is started when CRP level $\geq 20$ mg/l is detected in two consecutive recordings. Vehicle solution is administered to control animals. The condition of the animals is evaluated using an overall clinical score (0=no clinical signs of arthritis, 0.5=fever (>0.5° C.), 1=apathy, decreased mobility and loss of appetite, 2=weight-loss, warm extremities and/or joints, pain but without soft tissue swelling (STS), 3=moderate redness and STS of joints, normal flexibility of extremities, 4=severe redness and STS of joints, with joint stiffness, 5=thus severe arthritis that euthanasia is indicated), and scoring the severity of CIA (the severity of soft tissue swelling, flexibility and crepitation scored on a scale of – to +++: – none, ± doubtful, + moderate, ++ severe, +++ extreme). All these parameters result in an overall clinical score of CIA severity which is a semi-quantitative scale.

Efficacy of Fully Human VAP-1 Antibodies in Treating Collagen Antibody Induced Arthritis in the VAP-1 Humanized Mouse The efficacy of the fully human antibodies on collagen antibody-induced arthritis in transgenic mice expressing human VAP-1 on the endothelium can be evaluated. A rapidly progressing arthritis is induced by injecting an antibody cocktail followed by intraperitoneal lipopolysaccharide three days later. Intravenous doses of 3, 10 or 30 mg kg$^{-1}$ of the fully human antibody are given to the mice on days 1, 3 and 7. The control animals receive vehicle. A reduction in arthritic disease, as evidenced by statistically significant reductions in arthritic scoring in comparison to controls, can be shown.

Efficacy of VAP-1 Antibody Treatment in a Humanized Mouse Model of Psoriasis

The recent establishment and validation of a humanized xenotransplantation model has provided a valuable tool for increasing the understanding of this disease and for testing new drug therapies (Nickoloff B J. Expert Opin. Investig. Drugs. (1999) 8: 393-401).

In this model, non-lesional full thickness skin biopsies from psoriatic patients are transplanted on to anaesthetized severe combined immunodeficiency (SCID) mice of approximately 7-9 weeks of age, as previously described (Wrone-Smith T. et al. J. Clin. Invest. (1996) 98:1878-1887). The animals are allowed to recover from surgery for at least 2-3 weeks prior to induction of disease. Human peripheral blood mononuclear cells (PBMC) are isolated from a blood sample taken at biopsy and activated with the superantigen SEB (Staphylococcal enterotoxin B). Injection of the activated PBMCs, either intravenously or intradermally into the xenograft, induces the disease.

The fully human VAP-1 antibody or vehicle is administered intravenously or subcutaneously. Both prophylactic and therapeutic dosing regimens of different duration are possible. In addition, labeled human T-cells can be injected intravenously following fully human VAP-1 antibody treatment in order to investigate the effect on cellular infiltration in more detail.

At the end of the treatment period the mice are sacrificed and the grafts are excised together with surrounding mouse skin and fixed in formalin or snap-frozen in nitrogen. Histology and immunohistochemistry is performed in order to score pathological changes like changes in epidermal thickness, cellular infiltration, and expression of adhesion molecules. A reduction in psoriatic disease, as evidenced by statistically significant reductions in scoring in comparison to controls, can be shown.

Efficacy of Fully Human VAP-1 Antibody in Treating Liver Inflammation Resulting from Administration of $CCl_4$ to the VAP-1 Humanized Mouse The effect of fully human VAP-1 antibody on liver inflammation and fibrosis is assessed in a murine model of liver fibrosis resulting from administration of $CCl_4$. Transgenic mice expressing human VAP-1 on the endothelium are injected with 0.25 µl/g of $CCl_4$ i.p. twice a week for 12 weeks. Extensive liver inflammation and scarring develop over 12 weeks but, following cessation of $CCl_4$ injections, the scarring resolves completely. The effectiveness of the fully human antibody dosed i.v. or i.p. at doses between 1 and 25 mg/kg twice weekly in preventing injury and resolving existing fibrosis using this model is investigated by scoring pathological and histological changes in the liver. A reduction in disease, as evidenced by statistically significant reductions in scoring in comparison to controls, can be shown.

Efficacy of VAP-1 Antibody Treatment in a Model of Acute Myocardial Infarction in the Anaesthetized Rabbit A left thoracotomy is performed in anaesthetized mechanically ventilated New Zealand white rabbits. The heart is exposed and the left coronary artery (LCA) isolated and occluded. The fully human VAP-1 antibody is administered intravenously 25 minutes after the start of occlusion. 5 minutes after antibody administration the occlusion is removed and the area is then reperfused for up to 6 hours. The animal is killed by an overdose of the used anaesthetic and the heart is removed and rinsed with saline. The LCA is again occluded and Monastral or Evans blue is perfused through the heart, colouring the myocardium but leaving the area at risk uncoloured. The heart is frozen and the left ventricle is cut into thin sections. The total slice sections and the area at risk are determined using an image analysis system. The sections are then incubated with a 1% triphenyl tetrazolium chloride (TTC) solution in phosphate buffered saline followed by incubation in 10% neutral buffered formalin. The viable myocardium is coloured red by the TTC incubation and the infarcted area is thus determined by measuring the unstained tissue area and is expressed as the percentage of the determined area at risk. A reduction in tissue damage, as evidenced by statistically significant reductions in the percentage of the area at risk in comparison to controls, can be shown.

Efficacy of VAP-1 Antibody Treatment in mBSA Induced Arthritis in Rabbits

Methylated bovine serum albumin (mBSA) dissolved in physiological saline is mixed with an equal volume of Freund's complete adjuvant, and an emulsion is prepared. New Zealand white rabbits are immunized by intradermal injection of the emulsion twice, fourteen days apart. Approximately 10 days after the second immunization, serum is collected from the animals, and an intradermal injection of a mBSA solution is administered. The animals showing positive skin reactions are selected, and they are randomly divided into treatment groups, based on the serum titers of anti-mBSA IgG.

14 days after the second immunization VAP-1 antibody or vehicle is administered intravenously or subcutaneously, just prior to injection of mBSA solution into the joint cavity of the right knee. The left knee of each animal is injected with physiological saline. VAP-1 antibody or negative control injections are administered once or twice a week throughout the study.

From the day of induction (day 0), the rabbits are observed for behavior and external appearance by inspection and palpation daily and body weights are recorded at specified intervals throughout the study. Knee joint swelling is assessed at predetermined time-points by comparing the diameter of the inflamed (right) and non-inflamed (left) knees.

At the end of the experimental part of the study (day 21) the animals are sacrificed. Synovial fluid is collected for determination of total white blood cell number and protein content. The synovial membrane of each animal is dissected from the knee joints and divided longitudinally into two specimens at the site of the patella. One is deep-frozen in liquid nitrogen for the determination of VAP-1 antibody and VAP-1 expression, and the other specimens of synovial membrane and residual knee joint tissues are fixed in 10% neutral buffered formalin for staining with hematoxylin and eosin (HE), and phosphotungstic acid-hematoxylin (PTAH). The HE-stained sections are assessed for inflammatory reactions, and the PTAH-stained sections are assessed for the degree of fibrin deposit on the surface of the synovial membrane. A reduction in arthritic disease, as evidenced by statistically significant reductions in scoring in comparison to controls, can be shown.

In conclusion, these examples demonstrate that the fully human anti-VAP-1 antibodies retained the specific VAP-1 recognition properties of anti-VAP-1 antibodies (Example 2 and 6), blocked the VAP-1 dependent transmigration of leukocytes through endothelium (Example 7) and had improved pharmacokinetic properties compared to previous anti-VAP-1 monoclonal antibodies (Example 8).

It will be obvious to a person skilled in the art that, as the technology advances, the inventive concept can be implemented in various ways. The invention and its embodiments are not limited to the examples described above but may vary within the scope of the claims.

The invention claimed is:

1. A method of treating a condition involving an inflammatory reaction in which VAP-1 adhesion plays a role in mediating the transmigration and infiltration of leukocytes from the blood into a site of inflammation, said method comprising:

administering to a patient who has an inflammatory reaction in which VAP-1 adhesion plays a role in mediating the transmigration and infiltration of leukocytes from the blood into a site of inflammation an efficient amount of a pharmaceutical composition comprising a fully human anti-VAP-1 antibody or VAP-1 binding fragment thereof, comprising a heavy chain polypeptide, wherein the heavy chain polypeptide comprises, in the following order, the CDR sequences set forth as SEQ ID NOS: 1, 2, and 3 and a light chain polypeptide, wherein the light chain polypeptide comprises, in the following order, the CDR sequences set forth as SEQ ID NOS: 24, 25, and 26, characterized in that it is fully human.

2. The method according to claim 1, wherein said condition is selected from the group consisting of arthritides and connective tissue diseases, inflammatory bowel diseases, dermatoses, multiple sclerosis, inflammatory neuropathy, inflammatory myopathy, acute disseminated encephalomyelitis, vasculitis of the central nervous system, Sjogrens syndrome, diabetes, systemic lupus erythematosus, asthma, inflammatory liver disease, Graves disease and thyroiditis.

3. The method according to claim 2, wherein said arthritides and connective tissue disease is selected from the group consisting of reactive arthropathies, postinfective arthropathies, inflammatory polyarthropathies, systemic connective tissue disorders, inflammatory spondylopathies, myositis, synovitis, Reiter's disease, seropositive rheumatoid arthritis, other rheumatoid arthritis, extraarticular rheumatoid disease, psoriatic and enteropathic arthropathies, juvenile arthritis, unspecified arthritis, polyarteritis nodosa and related conditions, other necrotizing vasculopathies, dermatopolymyositis, systemic sclerosis, other systemic involvement of connective tissue, ankylosing spondylitis and inflammatory spondylopathies.

4. The method according to claim 2, wherein said inflammatory bowel disease is selected from the group consisting of Crohn's disease and ulcerative colitis.

5. The method according to claim 2, wherein said dermatoses is selected from the group consisting of Bullous disorders, dermatitis, papulosquamous disorders, erythema, lichen sclerosus et atrophicus, craurosis vulvae, discoid lupus erythematosus, morphea, Pemphigus, pemphigoid, dermatitis herpetiformis, atopic dermatitis, allergic contact dermatitis, irritant contact dermatitis, unspecified contact dermatitis, psoriasis and erythema multiforme.

6. The method according to claim 1, wherein said condition is selected from the group consisting of atherosclerosis, inflammation of the eye including uveitis, iritis, iridocyclitis, alcoholic hepatitis, allograft transplantation, xenograft transplantation, glomerulonephritis, reperfusion injury and acute inflammatory conditions following myocardial infarction and stroke.

7. The method of claim 2, wherein said condition is inflammatory liver disease.

8. The method of claim 1, wherein the antibody or fragment thereof is administered intravascularly or subcutaneously.

9. The method of claim 7, wherein the antibody is administered intravascularly.

10. The method of claim 7, wherein the antibody is administered at intervals ranging between once weekly to every three months.

11. The method of claim 9, wherein the antibody is administered at intervals ranging between once weekly to every three months.

* * * * *